(12) United States Patent
Backes et al.

(10) Patent No.: US 9,131,716 B2
(45) Date of Patent: Sep. 15, 2015

(54) USE OF NEOFLAVONOIDS FOR FLAVOR MODIFICATION

(75) Inventors: Michael Backes, Holzminden (DE);
Tobias Vössing, Beverungen (DE);
Jakob Peter Ley, Holzminden (DE);
Susanne Paetz, Höxter (DE)

(73) Assignee: SYMRISE AG, Holzminden (DE)

( * ) Notice: Subject to any disclaimer, the term of this patent is extended or adjusted under 35 U.S.C. 154(b) by 166 days.

(21) Appl. No.: 13/616,037

(22) Filed: Sep. 14, 2012

(65) Prior Publication Data

US 2013/0078192 A1     Mar. 28, 2013

Related U.S. Application Data

(60) Provisional application No. 61/535,115, filed on Sep. 15, 2011.

(30) Foreign Application Priority Data

Sep. 15, 2011 (EP) .................................. 11181504

(51) Int. Cl.
| | |
|---|---|
| A23L 1/226 | (2006.01) |
| A61K 8/49 | (2006.01) |
| A61K 47/22 | (2006.01) |
| A23L 1/22 | (2006.01) |

(52) U.S. Cl.
CPC .......... *A23L 1/22664* (2013.01); *A23L 1/22075* (2013.01); *A23L 1/22657* (2013.01); *A23L 1/22671* (2013.01); *A61K 8/498* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 7,005,146 B2 * | 2/2006 | Lee ............................... | 424/725 |
| 2008/0176912 A1 | 7/2008 | Kuo et al. | |
| 2010/0227039 A1 | 9/2010 | Ungureanu et al. | |

FOREIGN PATENT DOCUMENTS

| | | |
|---|---|---|
| DE | 2701280 A1 | 7/1978 |
| EP | 1258200 A2 | 11/2002 |

OTHER PUBLICATIONS

Russell S.J. Keast, Paul A.S. Breslin, "An overview of binary taste-taste interactions". Food Quality and Preference 14 (2002) 111-124.*
Abu T.M. Serajuddin. Salt formation to improve drug solubility. Advanced Drug Delivery Reviews 59 (2007) 603-616.*
Li Hongfang, Ma Qingyun, Liu Yuqing, Qian Jinfu, Zhou Jun & Zhao Youxing. Chemical Constituents from Polygonum perfoliatum. Chin J Appl Environ Biol 2009, 15 ( 5 ): 615-620.*
Drug Relevant Properties Prediction for compounds 7/8 from OSIRIS Property Explorer; downloaded Oct. 27, 2014 from the site: http://www.rdchemicals.com/drug-relevant-properties.html.*
Roelens F et al., "Regioselective synthesis and estrogenicity of (+/−)-8-alkyl-5,7-dihydroxy-4-(4-hydroxyphenyl)-3,4-dihydrocoumarins", European Journal of Medicinal Chemistry, Editions Scientifique Elsevier, Paris, FR, vol. 40, No. 10, 2005, pp. 1042-1051, XP027857667.
Sun Xingzhong et al.,"Neoflavonoids from *Polygonum* perfoliatum", Planta Medica, vol. 65, No. 7, 1999, pp. 671-673, XP002676796.
European Search Report, European Application No. 11181504.9, dated Jun. 18, 2012.

* cited by examiner

*Primary Examiner* — Frederick Krass
*Assistant Examiner* — Michael P Cohen
(74) *Attorney, Agent, or Firm* — Novak Druce Connolly Bove + Quigg LLP

(57) ABSTRACT

The present invention relates primarily to the use of one or a plurality of neoflavonoids of formula (I) and/or one or a plurality of physiologically acceptable salts of one or a plurality of neoflavonoids of formula (I) for flavor modification, in particular for altering or masking a bitter, astringent and/or metallic flavor impression of a bitter, astringent and/or metallic tasting substance and a corresponding method of flavor modification. The present invention further relates to certain mixtures and certain preparations fit for consumption containing one or a plurality of neoflavonoids of formula (I) and/or one or a plurality of physiologically acceptable salts of one or a plurality of neoflavonoids of formula (I).

6 Claims, No Drawings

USE OF NEOFLAVONOIDS FOR FLAVOR MODIFICATION

The present invention relates primarily to the use of one or a plurality of neoflavonoids of formula (I) defined hereunder and/or one or a plurality of physiologically acceptable salts of one or a plurality of neoflavonoids of formula (I) defined hereunder for flavor modification, in particular for altering or masking a bitter, astringent and/or metallic flavor impression of a bitter, astringent and/or metallic tasting substance and a corresponding method of flavor modification. The present invention further relates to certain mixtures and certain preparations fit for consumption containing one or a plurality of neoflavonoids of formula (I) and/or one or a plurality of physiologically acceptable salts of one or a plurality of neoflavonoids of formula (I).

Further aspects can be seen from the following description, the exemplary embodiments and the claims.

Foodstuffs or semi-luxury food products often contain a large number of various bitter substances, which certainly on the one hand are desirable in moderation in certain foodstuffs and contribute to their characteristic taste (e.g. caffeine in tea or coffee, quinine in so-called bitter-lemon beverages, bitter substances from hops in beer), on the other hand they may also greatly reduce the value (e.g. flavonoid glycosides and limonoids in citrus fruit juices, bitter aftertaste of many high-intensity sweeteners such as aspartame, cyclamate, acesulfame K, rebaudioside A, glycyrrhizin acid or saccharin, hydrophobic amino acids and/or peptides in cheese).

Bitter taste is regularly produced by certain substances (see below for examples), which bind to special bitter taste receptors on gustatory cells (which are to be found in the so-called taste buds on the tongue) and, via neurochemical cascades, send a signal to the brain that produces a defense reaction and a negative flavor impression (cf. Wolfgang Meyerhof, Reviews of Physiology, Biochemistry and Pharmacology 2005, 154, 37-72).

Astringent taste is as a rule caused by precipitation of proline-rich proteins in the saliva by astringents, e.g. metal salts, polyphenols such as (gallo-)catechins, proanthocyanidins, other flavonoids or tannins. The homogeneous saliva that normally serves as "lubricant" then contains denatured proteins, which reduce the lubricity and thus leave a rough or dry feeling in the mouth, which is also perceived as astringent (Am. J. Clin. Nutr. 2005, 81, 330S-335S).

To reduce the content of bitter substances in foodstuffs, which are either already present in the starting material, for example as in citrus fruits, or form during processing, for example as in cheese-making, a subsequent treatment is therefore often necessary. This can either take place by extraction, as in the decaffeination of tea or coffee, or enzymatically, e.g. treatment of orange juice with a glycosidase to destroy the bitter naringin or to cleave gallic acid esters of catechins to the free catechins with esterases or the use of special peptidases in the maturation of cheese. This treatment increases product cost, produces waste products and also causes for example solvent residues and other residues (enzymes) in the products.

Therefore it is desirable to find substances that can effectively alter, reduce or even eliminate unpleasant flavor impressions, in particular bitter, astringent and/or metallic flavor impressions, without affecting the quality of a corresponding foodstuff or of a corresponding preparation fit for consumption by additional process steps.

Suppression of bitter taste is also particularly important for many active pharmaceutical ingredients. This can greatly increase the willingness of patients, in particular in the case of patients sensitive to bitter taste such as children, to take a pharmaceutical preparation orally. Many active pharmaceutical ingredients, for example aspirin, salicin, paracetamol, ambroxol, antibiotics such as oxafloxacin or quinine, and a large number of other pharmaceutically active compounds, have a pronounced bitter, astringent and/or metallic taste and/or aftertaste.

Moreover, various nonnutritive, high-intensity sweeteners also often have flavor-related problems. Because they are used at low concentration, they are indeed suitable for imparting sweetness to foodstuffs, but they often display flavor-related problems owing to time-intensity profiles that are different from sugar (e.g. sucralose, steviosides, cyclamate), a bitter and/or astringent aftertaste (e.g. acesulfame K, saccharin, stevioside, rebaudioside A, rebaudioside C) and/or pronounced additional flavor impressions (e.g. glycyrrhizin acid, ammonium salt). In particular in the case of sweet, calorie-free or almost calorie-free foodstuffs, for example beverages, that have been produced using said sweeteners, this unpleasant tang and/or aftertaste often reduces the sensory acceptance and therefore needs to be masked.

Some approaches to at least partial reduction of bitterness have already been described (e.g. in Chemosensory Perception 2008, 1(1): 58-77). Various approaches can be used for solving the problems: removal of the bitter substance from the foodstuff, for example as in the debittering of citrus fruit juices, the use of encapsulation systems or the masking of bitter-tasting compounds by means of other flavoring materials or aromatic substances, e.g. as with sweeteners (Recent Patents on Drug Delivery and Formulation, 2009, 3, 26-39). The approaches described all regularly display sometimes considerable limitations in use, such as non-naturalness, expensive raw materials, undesirable side-effects (e.g. simultaneous suppression of sweetness, simultaneous salty taste etc.) and/or solubility problems, so that there is still a need for masking substances, in particular solutions for masking bitter taste, that are natural, simple to use or that can be incorporated easily in orally consumable preparations.

The primary aim of the present invention was to find substances (individual substances or mixtures) that make it possible to alter or mask (i.e. decrease or suppress) a bitter, astringent and/or metallic flavor impression of unpleasant-tasting substances in preparations fit for consumption, in particular in foodstuffs and semi-luxury food products or pharmaceutical preparations.

Preferably the required substances should have a bitter-masking effect against various bitter substances. The required substances should preferably not, or not greatly, affect the other, desirable flavor impression of a preparation fit for consumption. Preferably the required substances should be usable in a wide product range and/or should be easily accessible.

The primary aim of the present invention is achieved by using one, two or a plurality of different compounds of formula (I)

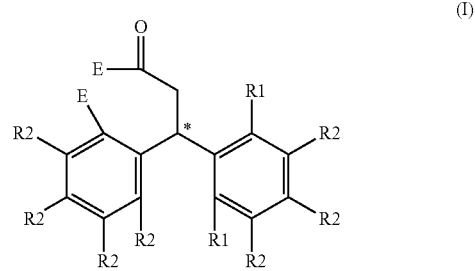

or one, two or a plurality of different physiologically acceptable salts of one, two or a plurality of different compounds of formula (I), or a mixture of one, two or a plurality of different compounds of formula (I) with one, two or a plurality of different physiologically acceptable salts of one, two or a plurality of different compounds of formula (I), wherein E either each denote OH or both E together denote an O, R1, in each case independently of the other residue R1, denotes hydrogen or $OR^a$, wherein $R^a$ is hydrogen, C1-C5 alkyl or C2-C5 alkenyl, R2, independently of the other residues R2, denotes hydrogen or $OR^b$, wherein $R^b$ is hydrogen, C1-C5 alkyl or C2-C5 alkenyl, wherein optionally two directly adjacent residues R1 and/or R2 together represent a group $OCH_2O$, for sensorily altering or masking the unpleasant flavor impression, preferably the bitter, astringent and/or metallic flavor impression, of an unpleasant-tasting substance.

It was found, surprisingly, that the neoflavonoids of formula (I) to be used according to the invention, mixtures thereof and/or salts thereof (in each case as defined above) can mask, i.e. decrease or even completely suppress, unpleasant, in particular bitter, astringent and/or metallic flavor impressions of a large number of unpleasant-tasting substances and orally consumable preparations that contain one or a plurality of unpleasant, in particular bitter, astringent and/or metallic tasting substances. This also applies correspondingly to the preparations according to the invention described hereunder.

Mask or masking means, in the context of the present text, a reduction, i.e. a decrease, or complete suppression.

Altering or masking of an unpleasant flavor impression consequently regularly means a flavor improvement, in particular in relation to bitter, astringent and/or metallic flavor impressions.

The configuration on the chiral carbon atom of the compounds of formula (I) (i.e. at the position marked with "*" in the above structural formula (I)) can be (R) or (S). This also applies to the following account and to the structural formulas given below of the compounds to be used according to the invention.

The compounds of formula (I) can, in preferred configurations, be combined together as pure enantiomers or as mixtures of enantiomers in any desired ratio to one another. In a preferred configuration, the compounds of formula (I) are used in the form of racemic mixtures, i.e. as racemates.

Preferably R1 and R2 mean, independently of the respective other residue R1 and R2, hydrogen, hydroxyl or a residue selected from the group consisting of

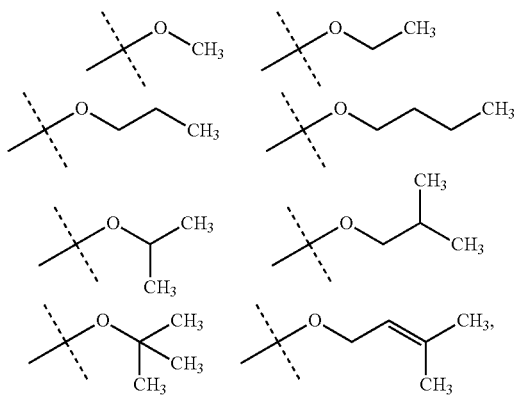

wherein the dashed line marks the bond that joins the residue to the adjacent carbon atom in formula (I).

Preferably, for the compounds of formula (I):

R1 denotes H or OH, and/or one or a plurality of the residues R1 or R2 in formula (I) mean a hydroxyl group.

The aforementioned use is preferred according to the invention, wherein one, two, a plurality of or all of the compounds used in each case are selected from the group consisting of the compounds of formula (I) and physiologically acceptable salts thereof, wherein E each denote OH or both E together denote oxygen, R1, in each case independently of the other residue R1, denotes hydrogen or hydroxyl, R2, independently of the other residues R2, denotes hydrogen, hydroxyl, methoxy, ethoxy, n-propoxy, iso-propoxy, n-butoxy, iso-butoxy, tert-butoxy or $OR^b$, wherein $R^b$ is C5 alkenyl, and more preferably $R^b$ denotes prenyl, wherein optionally two directly adjacent residues R2 together represent a group $OCH_2O$, wherein preferably one or a plurality of the residues R1 or R2 denote a hydroxyl group.

Preferably a compound of formula (I) has a total of one, two, three, four or five hydroxyl groups.

The compounds of formula (I) to be used according to the invention can, depending on the meaning of E, correspond to the following structural formulas (I-A) or (I-B), wherein R1 and R2 in each case have the meaning given above:

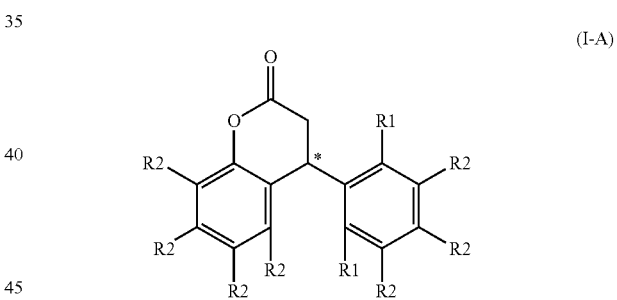

(I-A)

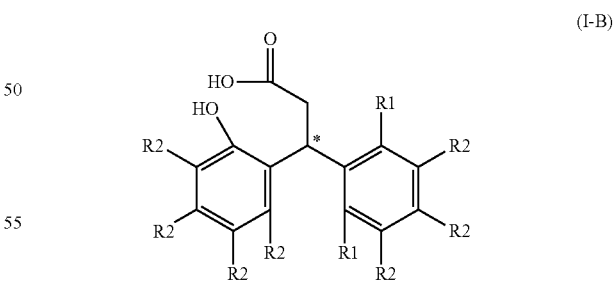

(I-B)

Depending on the pH, the lactone ring of the compound of formula (I-A) can be opened and the compound of formula (I-A) can be in equilibrium with the corresponding "open-chain" compound of formula (I-B), as shown schematically below, wherein $M^+$ denotes a (preferably physiologically acceptable) oppositely charged cation (and wherein the oppositely charged cation preferably has the meaning given below):

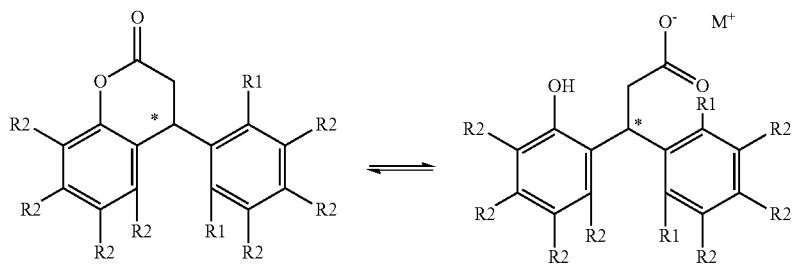

For the case when at least one of the two residues R1 in formula (I) denotes a hydroxyl group, depending on the (foodstuff) matrix and its pH—in particular in media or matrices with weakly acid pH—in most cases an equilibrium can be observed between the substances of formula (I-A1) and (I-A2).

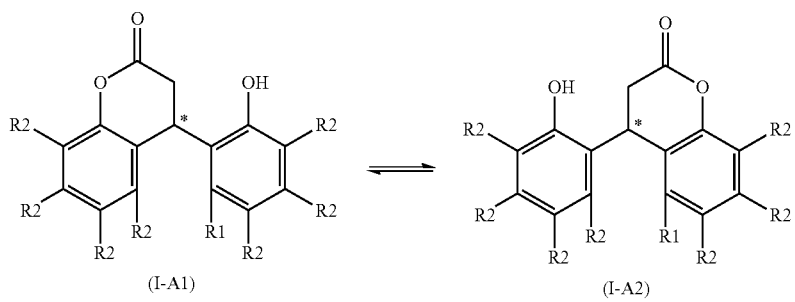

Another aspect of the present invention relates to the use of a mixture of substances comprising one or a plurality of compounds of formula (I-A1) and one or a plurality of compounds of formula (I-A2), and/or physiologically acceptable salts thereof.

Compounds of formula (I-A1) preferably to be used according to the invention are the substances (1) and (2)

(1) (4S)-5,7-dihydroxy-4-(2-hydroxyphenyl)chroman-2-one
(2) (4R)-5,7-dihydroxy-4-(2-hydroxyphenyl)chroman-2-one

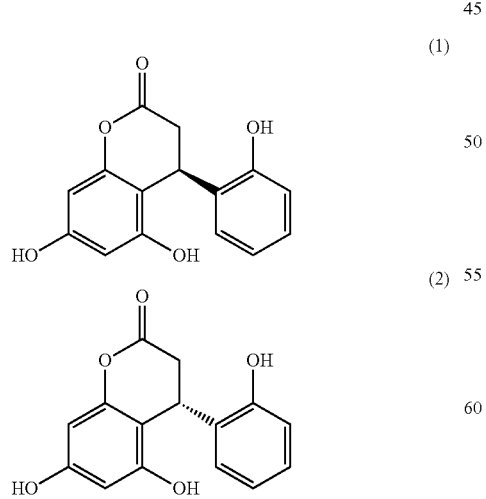

or
a salt of a compound of formulas (1) and (2)

or
a mixture of the compounds of formulas (1) and (2), two different salts of compounds of formulas (1) and (2) or a compound of formula (1) and (2) and a salt of compounds of formula (1) and (2), as flavor improver, preferably for masking or reducing unpleasant flavor impressions, in particular bitter, astringent and/or metallic flavor impressions.

The foregoing applies to the formation of isomeric compounds, depending on the foodstuff matrix and the pH.

Compounds of formula (I) are preferably used according to the invention that are in each case selected from the group consisting of the compounds of formula (II)

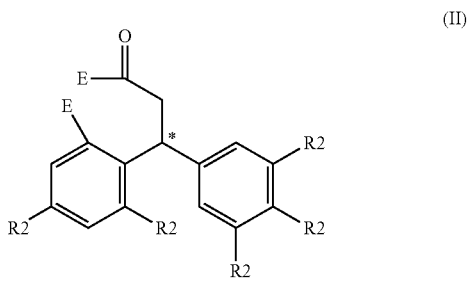

wherein
E each denote OH or both E together denote oxygen,
R2, independently of the other residues R2, denotes hydrogen, hydroxyl, methoxy, ethoxy, n-propoxy or iso-propoxy, preferably H, OH, $OCH_3$ or $OCH_2CH_3$,
wherein optionally two directly adjacent residues R2 together represent a group $OCH_2O$,
wherein preferably one or a plurality of the residues R2 denote a hydroxyl group,
and physiologically acceptable salts thereof.

Also preferable is the use of compounds of formula (II-A),

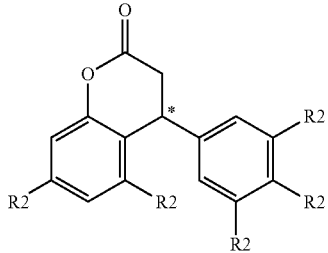

(II-A)

or
of a salt of a compound of formula (II-A)
or
of a mixture of two or a plurality of different compounds of formula (II-A), two or a plurality of different salts of compounds of formula (II-A) or of one or a plurality of different compounds of formula (II-A) and one or a plurality of different salts of one or a plurality of different compounds of formula (II-A),
wherein
R2, independently of the other residues R2, denotes hydrogen, hydroxyl, methoxy, ethoxy, n-propoxy or iso-propoxy, preferably H, OH, $OCH_3$ or $OCH_2CH_3$,
wherein optionally two directly adjacent residues R2 together represent a group $OCH_2O$,
wherein preferably at least one of the residues R2 denotes a hydroxyl group.

The configuration on the chiral carbon atom (i.e. at the position marked with "*" in the above formulas (II) and (II-A)) can in each case be (R) or (S).

Preferably a compound of formula (II) or a compound of formula (II-A) has a total of one, two, three, four or five hydroxyl groups, more preferably a total of one, two, three or four hydroxyl groups, particularly preferably a total of two, three or four hydroxyl groups.

It is particularly preferable according to the invention to use one or a plurality of compounds of formulas (3)-(28) and/or physiologically acceptable salts thereof
(3) (4S)-5,7-dihydroxy-4-(3-hydroxy-4-methoxyphenyl)chroman-2-one
(4) (4R)-5,7-dihydroxy-4-(3-hydroxy-4-methoxyphenyl)chroman-2-one
(5) (4S)-5,7-dihydroxy-4-(4-hydroxy-3-methoxyphenyl)chroman-2-one
(6) (4R)-5,7-dihydroxy-4-(4-hydroxy-3-methoxyphenyl)chroman-2-one
(7) (4S)-5,7-dihydroxy-4-(4-hydroxyphenyl)chroman-2-one
(8) (4R)-5,7-dihydroxy-4-(4-hydroxyphenyl)chroman-2-one
(9) (4S)-5,7-dihydroxy-4-(4-methoxyphenyl)chroman-2-one
(10) (4R)-5,7-dihydroxy-4-(4-methoxyphenyl)chroman-2-one
(11) (4S)-4-(1,3-benzodioxol-5-yl)-5,7-dihydroxy-chroman-2-one
(12) (4R)-4-(1,3-benzodioxol-5-yl)-5,7-dihydroxy-chroman-2-one
(13) (4S)-4-(3,4-dimethoxyphenyl)-5,7-dihydroxy-chroman-2-one
(14) (4R)-4-(3,4-dimethoxyphenyl)-5,7-dihydroxy-chroman-2-one
(15) (4S)-4-(3,4-dihydroxyphenyl)-5,7-dihydroxy-chroman-2-one
(16) (4R)-4-(3,4-dihydroxyphenyl)-5,7-dihydroxy-chroman-2-one
(17) (4S)-7-hydroxy-4-(4-hydroxyphenyl)chroman-2-one
(18) (4R)-7-hydroxy-4-(4-hydroxyphenyl)chroman-2-one
(19) (4S)-5-hydroxy-4-(4-hydroxy-3-methoxyphenyl)-7-methoxy-chroman-2-one
(20) (4R)-5-hydroxy-4-(4-hydroxy-3-methoxyphenyl)-7-methoxy-chroman-2-one
(21) (4S)-7-hydroxy-4-(4-hydroxy-3-methoxyphenyl)-5-methoxy-chroman-2-one
(22) (4R)-7-hydroxy-4-(4-hydroxy-3-methoxyphenyl)-5-methoxy-chroman-2-one
(23) (4S)-7-hydroxy-4-(4-hydroxy-3-methoxyphenyl)chroman-2-one
(24) (4R)-7-hydroxy-4-(4-hydroxy-3-methoxyphenyl)chroman-2-one
(25) (4S)-7-hydroxy-4-(3-hydroxy-4-methoxyphenyl)chroman-2-one
(26) (4R)-7-hydroxy-4-(3-hydroxy-4-methoxyphenyl)chroman-2-one
(27) (4S)-4-(3,4-dihydroxyphenyl)-7-hydroxy-chroman-2-one
(28) (4R)-4-(3,4-dihydroxyphenyl)-7-hydroxy-chroman-2-one The structural formulas of the compounds preferably to be used according to the invention (3) through (28) are given hereunder for clarification:

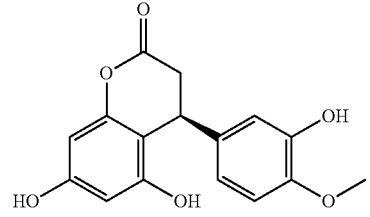

(3)

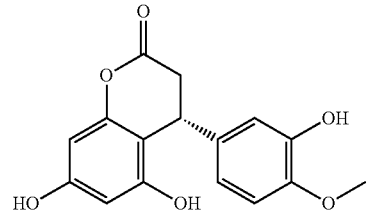

(4)

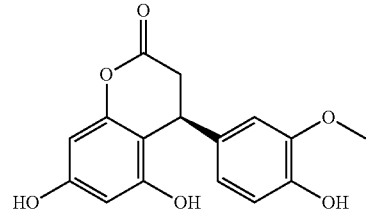

(5)

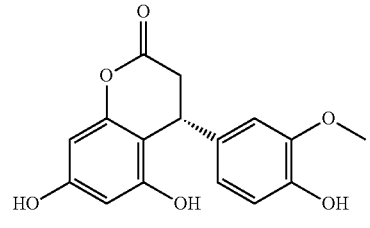

(6)

-continued (7)

(8)

(9)

(10)

(11)

(12)

(13)

-continued (14)

(15)

(16)

(17)

(18)

(19)

(20)

(21)
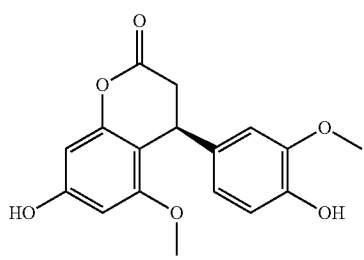

(22)
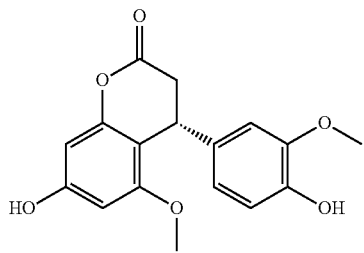

(23)
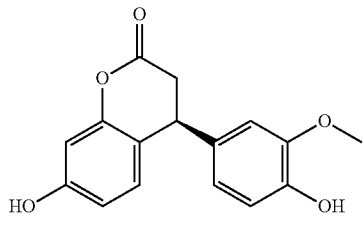

(24)
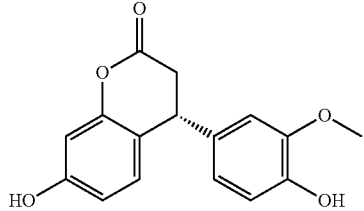

(25)
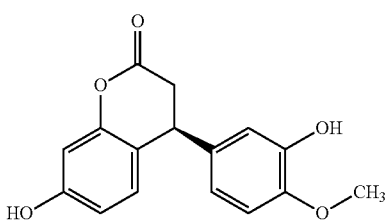

(26)
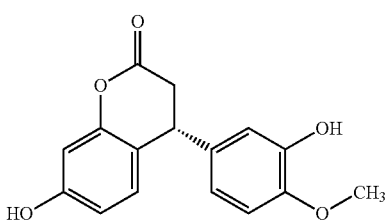

(27)
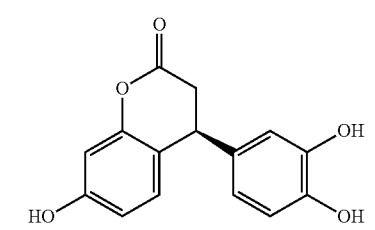

(28)
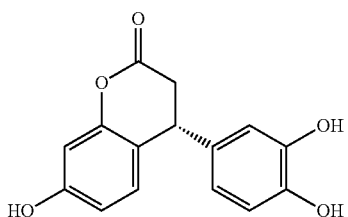

For the case when in an individual case there may be a discrepancy between the chemical nomenclature given above and the structural formula shown in each case for the compounds of formulas (1) through (28) preferably to be used according to the invention, the structural formula applies.

Various neoflavonoids of formula (I) may also occur in certain plants or parts of plants.

The neoflavonoids (7) and (8) and the neoflavonoids (29), (30), (31), (32), (33) and (34) that are also covered by general formula (I), which were found in *Polygonum perfoliatum* (see Planta Medica 1999, 65, 671-673; Chin. J. Appl. Environ. Biol. 2009, 15, 615-620) and physiologically acceptable salts thereof, are particularly preferred here.

(29)
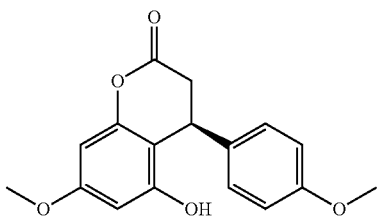

(30)
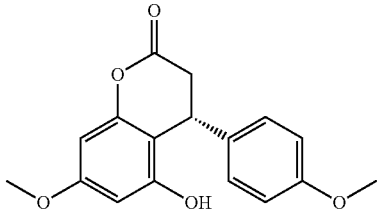

(31)
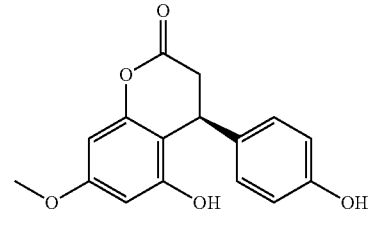

(32)
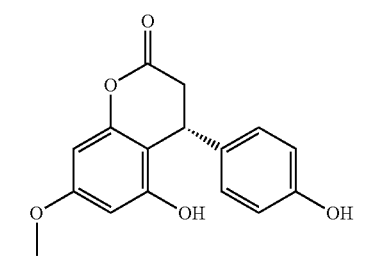

(33)

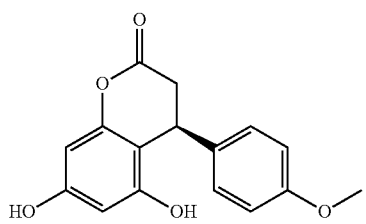

(34)

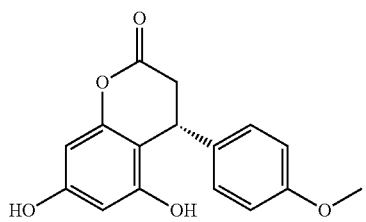

Accordingly, one or a plurality of the neoflavonoids of formula (I) that are to be used according to the invention can also be used according to the invention in the form of plant extracts, in particular in the form of plant extracts of *Polygonum perfoliatum*.

It is also preferable according to the invention to use the neoflavonoids (35), (36), (37) and (38) of the following structural formulas or physiologically acceptable salts thereof.

(35)

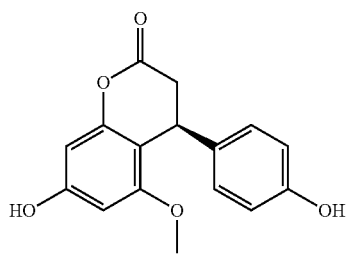

(36)

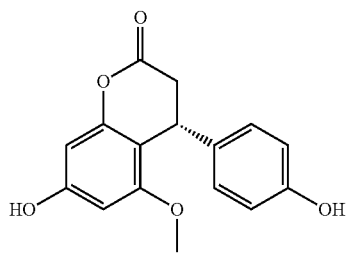

(37)

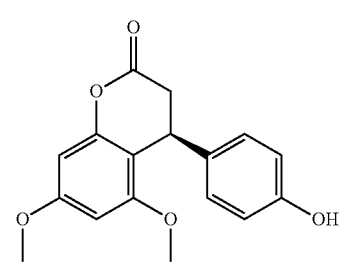

(38)

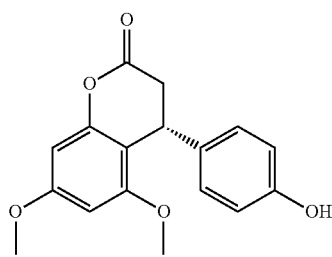

A chemist knows a plurality of routes for preparing the compounds of formula (I). A particularly preferred route is the acid-catalyzed reaction (classically, e.g. using sulfuric acid or hydrochloric acid) of phenol derivatives of the following formula (A) with cinnamic acid derivatives of the following formula (B) or of the corresponding esters of the following formula (C) to the compounds of formula (I) (as defined above), as outlined in the following scheme:

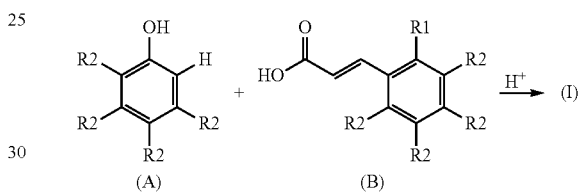

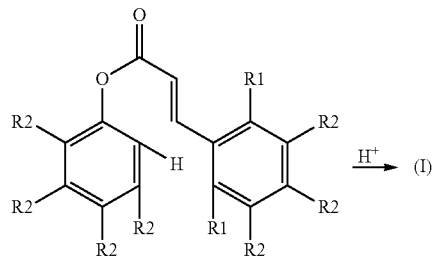

(C)

wherein in each case the residues R1 and R2 have the meaning given above with respect to formula (I).

More recent examples selected from the literature describe for example the use of silica-supported sulfuric acid under microwave irradiation (Guangzhou Huagong 2010, 38, 94-96), trifluoroacetic acid in dichloromethane (J. Org. Chem. 2005, 70, 2881-2883), montmorillonite K-10 in dioxane (Synthesis 2001, 15, 2247-2254) or p-toluenesulfonic acid, either in the bulk or with benzene or dichloromethane as solvent (Bull. Korean Chem. Soc. 2011, 32, 65-70).

Moreover, the neoflavanoids to be used according to the invention can also be prepared on the basis of the method described in Synth. Commun. 1987, 17(6) 723-727, as shown schematically below on the basis of the reaction of Meldrum's acid (E) with phloroglycinol (D) with addition of an aldehyde (e.g. para-hydroxybenzaldehyde (F)) in the presence of pyridine to produce a racemic mixture of compounds (7) and (8) to be used according to the invention.

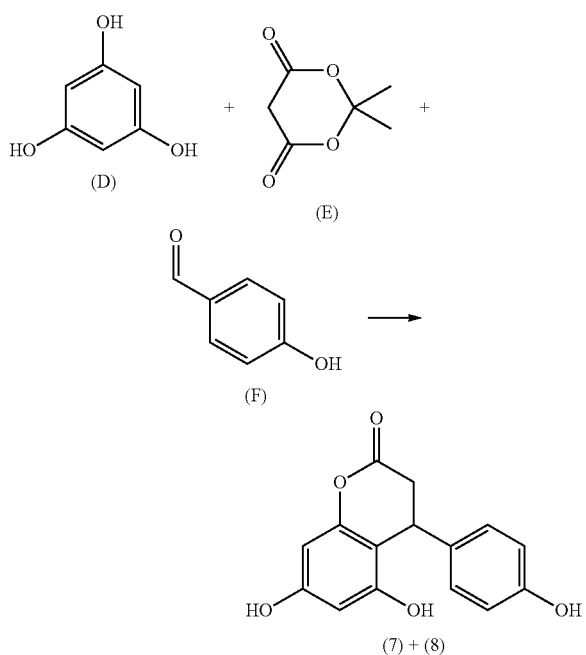

Medicinal properties of various substances of general structural formula (I) are described in the literature. For example, in CN 101906090, the compound (39) is tested as effective against the BGC823 cancer cell line. Moreover, the derivative (40) displayed strong cytotoxicity against Caco-2 cells (Chem. Pharm. Bull. 2010, 58, 242-246).

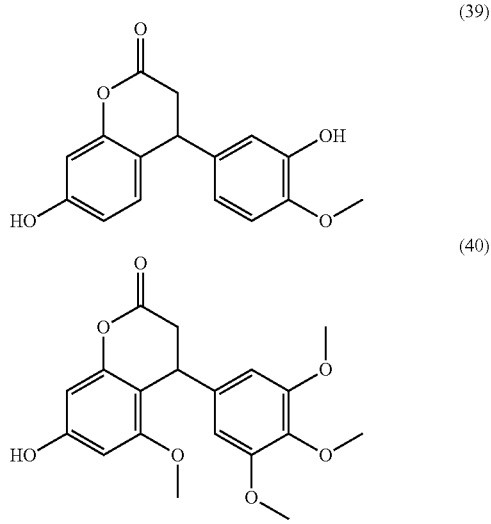

However, the flavor of the compounds of general formula (I) or the flavor-modifying properties of these compounds are not described in any publication.

Therefore in a preferred configuration the invention relates to the use of a compound of formulas (1)-(40), preferably a compound of formulas (3)-(28), or of a salt of a compound of formulas (1)-(40), preferably of a compound of formulas (3)-(28), or of a mixture of two or a plurality of different compounds of formulas (1)-(40), preferably a compound of formulas (3)-(28), or of a mixture of two or a plurality of different salts of compounds of formulas (1)-(40), preferably of a compound of formulas (3)-(28), or of a mixture of one or a plurality of different compounds of formulas (1)-(40), preferably a compound of formulas (3)-(28), and one or a plurality of different salts of one or a plurality of different compounds of formulas (1)-(40), preferably of a compound of formulas (3)-(28), as flavor improver, preferably for masking or reducing unpleasant flavor impressions, in particular bitter, astringent and/or metallic flavor impressions.

The compounds of formulas (I), (I-A), (I-A2), (I-B), (II) and (II-A) according to the invention can preferably be in the form of monovalent, or (especially in the case when a plurality of hydroxyl groups are present) polyvalent anions, wherein the cations with unipositive charge of the first main group and subgroup, the ammonium ion ($NH_4^+$), a trialkylammonium ion, the divalently charged cations of the second subgroup, and the trivalent cations of the 3rd main group and subgroup serve as oppositely charged cation. Preferably one, a plurality of or all oppositely charged cations are selected from the group consisting of $Na^+$, $K^+$, $NH_4^+$, $Ca^{2+}$, $Mg^{2+}$, $Al^{3+}$ and $Zn^{2+}$.

Surprisingly, it was found that compounds of general formula (I), mixtures and/or salts thereof (as defined above) in particular in the form of the mixtures and flavoring compositions according to the invention described hereunder, can alter, reduce or even completely suppress a bitter, astringent and/or metallic impression of a large number of unpleasant-tasting substances and orally consumable preparations that contain one or a plurality of bitter, astringent and/or metallic tasting substances.

Unpleasant-tasting substances in the context of this text are:

(a) substances that taste bitter, astringent, sticky, chalky, dusty, dry, mealy, rancid and/or metallic and (b) substances that have a bitter, astringent, sticky, chalky, dusty, dry, mealy, rancid and/or metallic aftertaste.

The aforementioned unpleasant tasting substances can possess further, not unpleasant taste and/or odor qualities. In the context of this text, as taste qualities that are not unpleasant preferably the impressions spicy, umami, sweet, salty, sour, sharp, cooling, warming, burning or tingling are to be mentioned.

Substances that taste bitter, astringent, sticky, chalky, dusty, dry, mealy, rancid and/or metallic are for example: xanthine alkaloids xanthines (caffeine, theobromine, theophylline), alkaloids (quinine, brucine, strychnine, nicotine), phenolic glycosides (e.g. salicin, arbutin), flavanoid glycosides (e.g. neohesperidin, eriocitron, neoeriocitrin, narirutin, hesperidin, naringin), chalcone or chalcone glycosides, dihydrochalcone glycosides (phloridzin, trilobatin), hydrolyzable tannins (gallic or ellagic acid esters of carbohydrates, e.g. pentagalloylglucose), nonhydrolyzable tannins (optionally galloylated catechins or epicatechins and oligomers thereof, e.g. proanthyocyanidin or procyanidin, thearubigenin), flavones and glycosides thereof (e.g. quercetin, quercitrin, rutin, taxifolin, myricetin, myrictrin), other polyphenols (γ-oryzanol, caffeic acid or esters thereof), terpenoid bitter substances (e.g. limonoids such as limonin or nomilin from citrus fruits, lupolones and humolones from hops, iridoids, secoiridoids), absinthin from wormwood, amarogentin from gentian, metallic salts (potassium chloride, sodium sulfate, magnesium salts, iron salts, aluminum salts, zinc salts), active pharmaceutical ingredients (e.g. fluoroquinolone antibiotics, paracetamol, aspirin, β-lactam antibiotics, ambroxol, propylthiouracil [PROP], guaifenesin), vitamins (for example vitamin H, B vitamins such as vitamin B1, B2, B6, B12, niacin, pantothenic acid), denatonium benzoate or other denatonium salts, sucralose octaacetate, urea, unsaturated fatty acids, in particular unsaturated fatty acids in emulsions, amino acids (e.g. leucine, isoleucine, valine, tryptophan, proline, histidine, tyrosine, lysine or phenylalanine), peptides (in particular peptides with an amino acid from the group leucine, isoleucine, valine, tryptophan, proline or phenylalanine on the N- or C-terminus). The aforementioned substances can either be present individually or as a mixture, preferably also as natural extracts of fresh, dried, roasted, and/or fermented plants or parts of plants, for example as extracts of leaves, fruits, branches, roots, fruit peel, kernels, seeds e.g. derived from *Camellia sinensis, Camellia japonica, Coffea* ssp., *Cocoa theobroma, Vitis vinifera, Citrus* ssp. and hybrids, *Poncirus* ssp. and hybrids, *Perilla, Humulus lupulus*, or related species.

Bitter substances to be masked according to the invention are in particular xanthines (in particular caffeine, theobromine, theophylline), phenolic glycosides (in particular salicin, arbutin), flavanoid glycosides (in particular neohesperedin, eriocitrin, neoeriocitrin, narirutin, hesperidin, naringin), chalcone or chalcone glycosides, dihydrochalcone glycosides (in particular phloridzin, trilobatin), hydrolyzable tannins (in particular gallic or ellagic acid esters of carbohydrates, e.g. pentagalloyl glucose), nonhydrolyzable tannins (in particular galloylated catechins or epicatechins and oligomers thereof, e.g. proanthyocyanidin or procyanidin, thearubigenin), flavone and glycosides thereof (in particular quercetin, quercitrin, rutin, taxifolin, myricetin, myrictrin), caffeic acid or esters thereof, terpenoid bitter substances (in particular limonin, nomilin, lupolones and humolones), metallic salts (potassium chloride, sodium sulfate, magnesium salts, iron salts, aluminum salts, zinc salts), active pharmaceutical ingredients (e.g. fluoroquinolone antibiotics, paracetamol, aspirin, β-lactam antibiotics, ambroxol, propylthiouracil [PROP], guaifenesin), amino acids (e.g. leucine, isoleucine, valine, tryptophan, proline, histidine, tyrosine, lysine or phenylalanine), peptides (in particular peptides with an amino acid from the group leucine, isoleucine, valine, tryptophan, proline or phenylalanine on the N- or C-terminus).

Other bitter substances preferably to be masked according to the invention are selected from the group consisting of caffeine, theobromine, quinine, salicin, arbutin, neohesperedin, eriocitrin, neoeriocitrin, narirutin, hesperidin, naringin, phloridzin, catechin, epicatechin, epigallocatechin gallate (EGCG), gallocatechin, gallocatechin-3-gallate, procyanidin B2, procyanidin B5, procyanidin C1, thearubigenin, rutin, taxifolin, myricetin, myrictrin, caffeic acid or esters thereof, limonin and nomilin, amino acids (e.g. leucine, isoleucine, valine, tryptophan, proline, histidine, tyrosine, lysine or phenylalanine), peptides with an amino acid from the group leucine, isoleucine, valine, tryptophan, proline or phenylalanine on the N- or C-terminus, potassium chloride, paracetamol, aspirin and β-lactam antibiotics.

Substances that have a bitter, astringent, sticky, chalky, dusty, dry, mealy, rancid and/or metallic tang and/or aftertaste can be aromatic substances or flavoring materials with a not unpleasant primary taste (for example sweet, salty, spicy, sour) and/or odor, and may belong for example to the group of sweeteners, sugar substitutes or aromatic substances. For example, we mention: aspartame, neotame, superaspartame, alitame, saccharin, sucralose, tagatose, monellin, monatin, steviosides, rubusoside, stevioside, rebaudioside A, rebaudiosides C, thaumatin, miraculin, glycyrrhizin (glycyrrhizin acid), glycyrrhetic acid or derivatives thereof, cyclamate or the physiologically acceptable salts of the aforementioned compounds.

The compounds of formula (I) to be used according to the invention and the physiologically acceptable salts of the compounds of formula (I) have, in preparations according to the invention that are fit for consumption, in particular at the concentrations to be used (particularly) preferably according to the invention, no notable intrinsic taste, in particular they do not display any unpleasant or interfering flavor notes at the (preferred or particularly preferred) concentrations used.

Compounds (1) through (40) are preferred according to the invention, and compounds (3) through (28) are further preferred, and mixtures and salts thereof defined above, wherein these can in each case be racemic mixtures, individual substances or can be combined in any proportions. Compounds (7) and (8) are in particular preferred, which can also be used according to the invention in the form of an extract of *Polygonum perfoliatum*.

If the compounds to be used according to the invention, in particular compounds (7) and (8), occur naturally, these can also be used in the form of a plant extract.

Accordingly, the present invention also relates to the use of a product obtainable or obtained from plant material by extraction comprising one, two or a plurality of different compounds of formula (I) as defined above, one, two or a plurality of different physiologically acceptable salts of one, two or a plurality of different compounds of formula (I) as defined above, or a mixture of one, two or a plurality of different compounds of formula (I) as defined above with one, two or a plurality of different physiologically acceptable salts of one, two or a plurality of different compounds of formula (I) as defined above, for sensorily altering or masking the unpleasant flavor impression, preferably the bitter, astringent and/or metallic flavor impression, of an unpleasant-tasting substance.

Said plant extract to be used according to the invention preferably contains a total proportion of 50 wt % or more, preferably of 80 wt % or more, particularly preferably of 90 wt % or more of the compounds of formula (I), preferably compounds (7) and (8), in each case relative to the dry weight of the plant extract, wherein the compounds of formula (I), preferably compounds (7) and/or (8), are either present as individual substances or can be combined in any proportions.

The present invention further relates to certain preparations that are fit for consumption either immediately or after further processing.

Preparations according to the invention can also be in the form of semifinished products, for example as a composition of odoriferous, aromatic or flavoring materials or as a condiment mixture.

The invention relates to a preparation fit for consumption, selected from the group consisting of preparations used for nutrition, as food supplements, for oral hygiene or for pleasure, cosmetic preparations, preferably for application in the region of the head, pharmaceutical preparations intended for oral administration, containing one, two or a plurality of unpleasant, in particular bitter, astringent and/or metallic tasting substances and one, two or a plurality of different compounds of formula (I) as defined above, or one, two or a plurality of different physiologically acceptable salts of one, two or a plurality of different compounds of formula (I) as defined above, or a mixture of one, two or a plurality of different compounds of formula (I) as defined above with one, two or a plurality of different physiologically acceptable salts of one, two or a plurality of different compounds of formula (I) as defined above, wherein the amount of the unpleasant, in particular bitter, astringent and/or metallic tasting substance or substances is sufficient to be perceived as an unpleasant, in particular bitter, astringent and/or metallic, taste in a comparative preparation, that contains neither a compound of formula (I) as defined above nor a salt of a compound of formula (I) as defined above, but otherwise is of identical composition, and the total amount of compounds of formula (I) as defined above, of salts of the compounds of formula (I) as defined above or of a mixture as defined above is sufficient for sensorily altering or masking, in comparison with the comparative preparation, the unpleasant, in particular bitter, astringent and/or metallic, flavor impression of the unpleasant-tasting substance or substances.

The aqueous-ethanolic extracts of the ground whole plant *Polygonum perfoliatum* described in Planta Medica 1999, 65, 671-673 and Chin. J. Appl. Environ. Biol. 2009, 15, 615-620, as well as the fractions and mixtures of substances obtained therein from the aqueous-ethanolic extracts, are not objects of the present invention.

A preferred preparation according to the invention is characterized in that the preparation is not an extract that is obtainable by extraction of the ground whole plant *Polygonum perfoliatum* with an extractant mixture of ethanol and water in the weight or volume ratio 90:10 or 95:5, and preferably is not an extract that is obtainable by extraction of the whole plant *Polygonum perfoliatum* with an extractant mixture of ethanol and water with a volume ratio greater than 1:1, and preferably is not an extract that is obtainable by extraction of the whole plant *Polygonum perfoliatum* with an extractant mixture of ethanol and water.

A preferred preparation according to the invention preferably does not contain hexane and does not contain methylene chloride, and preferably does not contain hexane, methylene chloride, acetone or methanol.

A preferred preparation according to the invention is not a preparation that contains 4-dihydroxy-5,7-dihydroxy-4-(4-hydroxyphenyl)coumarin, α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5, bonaroside, helonioside A, helonioside B, lapathoside D, vanicoside B, vanicoside C, vanicoside F, asteryunnanoside, saikosaponin M, hydropiperoside, quercetin-3-O-β-D-glucuronide-6''-butyl ester and quercetin-3-O-β-D-glucuronide-6''-methyl ester.

Regarding the structural formulas corresponding to these compounds, reference is made to the literature source Chin. J. Appl. Environ. Biol. 2009, 15, 615-620, which with respect to the corresponding compounds disclosed therein becomes part of this application by reference.

A preferred preparation according to the invention is not a preparation that contains 4-dihydroxy-5,7-dihydroxy-4-(4-hydroxyphenyl)coumarin, α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside in the proportions by weight of 4:9:8:37:30:24:14:5:12:41.

If a preparation according to the invention contains 4-dihydroxy-5,7-dihydroxy-4-(4-hydroxyphenyl)coumarin, one, a plurality of or all of the following conditions apply:

the weight ratio of 4-dihydroxy-5,7-dihydroxy-4-(4-hydroxyphenyl)coumarin to quercetin is not equal to 4:30, the weight ratio of 4-dihydroxy-5,7-dihydroxy-4-(4-hydroxyphenyl)coumarin to cucurbitacin IIa is not equal to 4:24, the weight ratio of 4-dihydroxy-5,7-dihydroxy-4-(4-hydroxyphenyl)coumarin to cucurbitacin U is not equal to 4:14, the weight ratio of 4-dihydroxy-5,7-dihydroxy-4-(4-hydroxyphenyl)coumarin to 7'-dihydroxymatairesinol is not equal to 4:8, and wherein preferably at least one of the unpleasant, in particular bitter, tasting substances contained in the preparation is not quercetin, is not cucurbitacin IIa, is not cucurbitacin U and is not 7'-dihydroxymatairesinol.

If a preparation according to the invention contains 4-dihydroxy-5,7-dihydroxy-4-(4-hydroxyphenyl)coumarin, the ratio of the mass of 4-dihydroxy-5,7-dihydroxy-4-(4-hydroxyphenyl)coumarin to the total mass of α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside is not 4:180.

A preferred preparation according to the invention is not a preparation that contains α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5, bonaroside, helonioside A, helonioside B, lapathoside D, vanicoside B, vanicoside C, vanicoside F, asteryunnanoside, saikosaponin M, hydropiperoside, quercetin-3-O-β-D-glucuronide-6''-butyl ester and quercetin-3-O-β-D-glucuronide-6''-methyl ester.

A preferred preparation according to the invention is not a preparation that contains α-tocopherol quinone, (24S)-ethylcholesta-3β,5α,6α-triol, cucurbitacin IIa, cucurbitacin U, iotroridoside A, pokeweedcerebroside 5 and bonaroside.

A preferred preparation according to the invention does not contain any cucurbitacin IIa, preferably does not contain any cucurbitacin IIa or any cucurbitacin U, and preferably does not contain any cucurbitacins.

The configurations described above, in particular the configurations characterized above as preferred or particularly preferred, with respect to the use according to the invention of the compounds of formulas (I), (I-A), (I-A1), (I-A2), (I-B), (II) and (II-A) apply correspondingly to a preparation according to the invention, in particular to a preferred or particularly preferred preparation according to the invention.

Preparations according to the invention, in particular preparations according to the invention fit for, preferably direct, consumption, preferably contain one or a plurality of further aromatic substances, flavoring materials and/or flavor correctants, for rounding off, improving or refining the taste and/or odor of the preparation. Suitable further aromatic substances, flavoring materials and/or flavor correctants are preferably synthetic or natural aromatic substances, flavoring materials and/or flavor correctants, and preferably saliva-promoting, tingling, sharp and/or hot tasting substances, essential oils or plant extracts, and optionally in addition auxiliaries and carriers that are fit for consumption. It is especially advantageous that the bitter, astringent and/or metallic flavor impression can additionally be altered and/or reduced by further aromatic substances, flavoring materials and/or flavor correctants so that the overall aroma or flavor profile of a preparation according to the invention is improved.

Preparations according to the invention preferably contain at least one, two, three, four, five, six, seven, eight, nine, ten or a plurality of further aromatic substances.

A preferred preparation according to the invention is characterized in that the preparation (i) contains one, two, three, four, five, six, seven, eight, nine, ten or a plurality of further aromatic substances with a molar weight above 90 g/mol, preferably above 100 g/mol, preferably with a molar weight in the range from 110 g/mol through 300 g/mol, more preferably with a molar weight in the range from 120 g/mol through 250 g/mol, particularly preferably with a molar weight in the range from 125 g/mol through 220 g/mol, in particular preferably with a molar weight in the range from 130 g/mol through 210 g/mol, and/or (ii) the preparation does not contain one, two, three, four, five, six, seven, eight or all of the following substances: tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside, and/or (iii) the preparation does not contain the following substances:
(24S)-ethylcholesta-3β,5α,6α-triol, iotroridoside A, pokeweedcerebroside 5, bonaroside, helonioside A, helonioside B, lapathoside D, vanicoside B, vanicoside C, vanicoside F, asteryunnanoside, hydropiperoside, and/or (iv) the preparation is free from fresh or dried parts of plants, in particular free from leaves and parts of leaves, of *Persicaria perfoliata* (=*Polygonum perfoliatum*).

A particularly preferred preparation according to the invention is characterized in that the preparation (i) contains two, three, four, five, six, seven, eight, nine, ten or a plurality of further aromatic substances with a molar weight above 120 g/mol, preferably with a molar weight above 125 g/mol, preferably with a molar weight in the range from 125 g/mol through 220 g/mol, particularly preferably with a molar weight in the range from 130 g/mol through 210 g/mol.

Preferably at least two of the conditions defined above apply, preferably condition (i) and (iv) or condition (i) and (iii).

Preferably at least three of the conditions defined above apply, preferably condition (i), (ii) and (iv) or condition (i), (ii) and (iii), or all the conditions (i) through (iv).

In the context of the present invention, (one or a plurality of) aromatic substances preferably to be used are preferably selected from the group consisting of:

acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene phthalide, carvone, camphene, caryophyllene, cineol, cinnamyl acetate, citral, citronellol, citronellal, citronellyl acetate, cyclohexyl acetate, cymene, damascone, decalactone, dihydrocoumarin, dimethyl anthranilate, dimethyl anthranilate, dodecalactone, ethoxyethyl acetate, ethylbutyric acid, ethyl butyrate, ethyl caprate, ethyl caproate, ethyl crotonate, ethylfuraneol, ethylguaiacol, ethylisobutyrate, ethylisovalerate, ethyl lactate, ethylmethyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzyl acetone, isoamyl alcohol, isoamyl isovalerate, isobutyl butyrate, isobutyraldehyde, isoeugenol methyl ether, isopropyl methylthiazole, lauric acid, levulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfurfural, 3,2,2-methylcyclopentenolone, 6,5,2-methylheptenone, methyl dihydrojasmonate, methyl jasmonate, 2-methylmethyl butyrate, 2-methyl-2-pentenol acid, methylthiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nootkatone, delta-octalactone, gamma-octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegon, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and its derivatives (here preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethylmaltol), coumarin and coumarin derivatives, gamma-lactones (here preferably gamma-undecalactone, gamma-nonalactone, gamma-decalactone), delta-lactones (here preferably 4-methyldeltadecalactone, massoilactone, deltadecalactone, tuberolactone), methyl sorbate, divanillin, 4-hydroxy-2(or 5)-ethyl-5(or 2)-methyl-3 (2H)furanone, 2-hydroxy-3-methyl-2-cyclopentenone, 3-hydroxy-4,5-dimethyl-2(5H)-furanone, acetic acid isoamyl ester, butyric acid ethyl ester, butyric acid-n-butyl ester, butyric acid isoamyl ester, 3-methyl-butyric acid ethyl ester, n-hexanoic acid ethyl ester, n-hexane acid allyl ester, n-hexanoic acid-n-butyl ester, n-octanoic acid ethyl ester, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulfide, furfurylmercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamon alcohol, methylsalicylate, isopulegol and (here not explicitly stated) stereoisomers, enantiomers, positional isomers, diastereomers, cis/trans isomers or epimers of these substances.

Preparations used for nutrition or for pleasure (i.e. fit for consumption) are in the context of this text e.g. baked products (e.g. bread, cookies, cakes, other baked goods), confectionery (e.g. chocolates, chocolate bar products, other bar products, fruit gums, hard and soft toffees, chewing gum), alcoholic or nonalcoholic beverages (e.g. coffee, tea, wine, wine-containing beverages, beer, beer-containing beverages, liqueurs, spirits, brandies, fruit-containing lemonades, isotonic beverages, refreshing beverages, nectars, fruit and vegetable juices, fruit or vegetable juice preparations), instant beverages (e.g. instant-cocoa beverages, instant-tea beverages, instant-coffee beverages), meat products (e.g. ham, sausage or raw-sausage preparations, spiced or marinated fresh or salted meat products), eggs or egg products (dried egg, egg white, egg yolk), cereal products (e.g. breakfast cereals, muesli bars, precooked prepared rice products), milk products (e.g. milk beverages, milk ices, yoghurt, kefir, fresh cheese, soft cheese, hard cheese, dried milk powder, whey, butter, buttermilk, partially or fully hydrolyzed lactoprotein-containing products), products from soybean protein or other soybean fractions (e.g. soybean milk and products prepared therefrom, preparations containing soybean lecithin, fermented products such as tofu or tempeh or products prepared therefrom, soy sauces), fruit preparations (e.g. jellies, fruit ices, fruit sauces, fruit fillings), vegetable preparations (e.g. ketchup, sauces, dried vegetables, frozen vegetables, precooked vegetables, vegetables pickled in vinegar, preserved vegetables), nibbles (e.g. baked or fried potato chips or potato dough products, bread dough products, extruded products based on maize or peanut), fat-based and oil-based products or emulsions thereof (e.g. mayonnaise, remoulade, dressings, condiment preparations), other ready-meals and soups (e.g. dry soups, instant soups, precooked soups), spices, condiment mixtures and in particular seasonings, which find application for example in the snack area. The preparations in the sense of the invention can also serve as semifinished products for making further preparations used for nutrition or pleasure. The preparations in the sense of the invention can also be in the form of capsules, tablets (uncoated and coated tablets, e.g. enteric coatings), sugar-coated pills, granules, pellets, solid mixtures, dispersions in liquid phases, as emulsions, as powders, as solutions, as pastes or as other preparations to be swallowed or chewed as food supplements.

It was found, surprisingly, that the compounds to be used according to the invention, mixtures thereof and/or salts thereof (in each case as defined above)—even at very low concentrations—can mask, i.e. reduce or even completely suppress, unpleasant taste impressions, in particular the bitter taste impression, of a large number of substances.

In a preferred preparation according to the invention, the total amount of compounds of formula (I) as defined above and of physiologically acceptable salts of the compounds of formula (I) as defined above is in the range from 0.1 mg/kg (corresponding to 0.1 ppm) through 1 wt %, preferably in the range from 0.5 through 1000 mg/kg (corresponding to 0.5 through 1000 ppm), preferably in the range from 1 through 500 mg/kg, more preferably in the range from 3 through 300 mg/kg, particularly preferably in the range from 5 through 200 mg/kg, most preferably in the range from 10 through 100 mg/kg, in each case relative to the total weight of the preparation.

As the bitterness intensity of different bitter substances varies widely, the bitterness of a compound is sometimes stated hereunder in relative bitterness equivalents (RBE). The reference substance used here is the known bitter substance caffeine. The RBE value as a measure for the relative bitterness of a sample is determined using a scale from 1 through 10. A relative bitterness of 1, i.e. an RBE value of 1, corresponds to the bitterness of an amount of caffeine at a dosage of 100 mg/kg of the test sample. A relative bitterness of 5, i.e. an RBE value of 5, corresponds to the bitterness of an amount of caffeine at a dosage of 500 mg/kg of the test sample. The test sample can vary widely in its composition. Thus, the test sample can be for example a preparation used for nutrition, for oral hygiene, for pleasure, an oral pharmaceutical preparation or a cosmetic preparation, for example a foodstuff, a beverage, a chewing gum, a mouthwash, a candy, a cough syrup or a tablet.

The scale used for determining the RBE values corresponds to ISO 4121 [Sensory Analysis—Guidelines for the use of quantitative response scales; A.3 Example 2].

The members of the panel for determining the RBE values are selected according to ISO 8586-1 [Sensory Analysis—General guidance for the selection, training, and monitoring of assessors—Part 1: Selected assessors].

The number of members of the panel corresponds to ISO 8586-I, 4.2.3 [Number of persons to be selected, together with ISO 6658 Sensory analysis—Methodology—General guidance—5.3.5 Scoring (5 or more selected members of the panel)].

A preparation preferred according to the invention is characterized in that
the or one of the unpleasant-tasting substances is a bitter substance, which is present at a concentration that corresponds to at least 2 relative bitterness equivalents,
or
a plurality of or all of the unpleasant-tasting substances are bitter substances, wherein the total concentration of all bitter substances corresponds to at least 2 relative bitterness equivalents.

A preparation preferred according to the invention is characterized in that
the total amount of compounds of formula (I) as defined above and of physiologically acceptable salts of the compounds of formula (I) as defined above is sufficient for sensorily altering or masking the unpleasant, in particular bitter, taste impression of the or the unpleasant, in particular bitter, astringent and/or metallic tasting substances, so that it corresponds to the taste impression of a comparative preparation, which (i) neither contains one of the above defined compounds of formula (I) nor a physiologically acceptable salt of a compound of formula (I) as defined above and (ii) contains 90 wt % or less, preferably 80 wt % or less, preferably 75 wt % or less, particularly preferably 70 wt % or less of the unpleasant-tasting substance or substances, but otherwise is of identical composition,
and/or
the or one of the unpleasant-tasting substances is a bitter substance, which is present at a concentration of at least double its bitterness threshold value, preferably in the range from three to a thousand times its bitterness threshold value.

In particular the bitter taste impression of methyl xanthines, for example caffeine, theobromine, alkaloids, such as quinine, flavonoids such as naringin, (gallo-)catechins and gallates thereof, (gallo-)epicatechins and gallates thereof, phenols such as arbutin, salicin, or also inorganic salts such as potassium chloride or magnesium sulfate can be masked, wherein it is especially advantageous that the compounds to be used according to the invention, mixtures thereof and/or salts thereof (in each case as defined above) possess hardly any intrinsic taste in the low concentrations preferably used.

A preferred preparation according to the invention contains one, two or a plurality of the following bitter substances:
catechins and proanthocyanidins in a total amount of at least 0.01 wt %, preferably of at least 0.05 wt %, preferably in the range from 0.075 wt % through 1 wt %,
caffeine and theobromine in a total amount of at least 0.005 wt %, preferably of at least 0.01 wt %, preferably of at least 0.02 wt %, more preferably in the range from 0.025 wt % through 1 wt %,
naringin at a concentration of at least 0.005 wt %, preferably of at least 0.01 wt %, preferably in the range from 0.02 wt % through 0.5 wt %,
sweeteners in a total amount of at least 0.005 wt %, preferably of at least 0.05 wt %, preferably in the range from 0.1 wt % through 2 wt %,
in each case relative to the total weight of the preparation.

The preparations used for oral hygiene are in the context of this text in particular oral and/or dental hygiene products such as toothpastes, dental gels, tooth powder, mouthwash, chewing gums and other oral hygiene products, containing at least one bitter tasting substance with an RBE of 2 or more.

Oral pharmaceutical preparations, in the context of this text, are preparations that are for example in the form of capsules, tablets (uncoated and coated tablets, e.g. enteric coatings), sugar-coated pills, granules, pellets, solid mixtures, dispersions in liquid phases, as emulsions, as powders, as solutions, as pastes or as other preparations to be swallowed or chewed and are used as prescription-only, pharmacy-only or other medicinal products or as food supplements and comprise at least one bitter tasting substance with an RBE of 2 or more.

Other usual active substances, base substances, auxiliaries and additives used for nutrition, for oral hygiene or for semi-luxury food products or oral pharmaceutical preparations can be contained in amounts of up to 99.9999999 wt %, relative to the total weight of the preparation. Moreover, the preparations can contain water in an amount up to 99.99 wt %, preferably 5 to 90 wt %, relative to the total weight of the preparation.

The preparations according to the invention, containing one or a plurality of compounds of formula (I) to be used according to the invention or salts or mixtures thereof, are produced according to a preferred configuration, by incorporating the compounds of formula (I) to be used according to the invention, salts or mixtures as pure substances, as solution or in the form of a mixture with a solid or liquid carrier in a preparation used for nutrition, for oral hygiene or for pleasure, or an oral pharmaceutical preparation. Advantageously, preparations according to the invention that are in the form of a solution can also be transformed by spray-drying into a solid preparation.

According to another preferred embodiment, for production of preparations according to the invention, the compounds of formula (I) to be used according to the invention or salts or mixtures thereof and optionally other constituents of the preparation according to the invention are also incorporated beforehand in emulsions, in liposomes, e.g. starting from phosphatidylcholine, in microspheres, in nanospheres or also in capsules, granules or extrudates from a matrix suitable for foodstuffs and semi-luxury food products, e.g. made from starch, starch derivatives, cellulose or cellulose derivatives (e.g. hydroxypropylcellulose), other polysaccharides (e.g. alginate), natural fats, natural waxes (e.g. beeswax, carnauba wax) or from proteins, e.g. gelatin.

In another preferred method of production for preparations according to the invention, the compounds of formula (I) to be used according to the invention, salts or mixtures are complexed beforehand with one or a plurality of suitable complexing agents, for example with cyclodextrins or cyclodextrin derivatives, preferably α- or β-cyclodextrin, and used in this complexed form.

An orally consumable preparation according to the invention is particularly preferred, in which the matrix is selected so that the release of the compounds of formula (I) to be used according to the invention, salts or mixtures from the matrix is delayed, thus giving a long-lasting action.

As further constituents for preparations according to the invention, used for nutrition or for pleasure, it is possible to use usual base materials, auxiliaries and additives for foods and semi-luxury food products, e.g. water, mixtures of fresh or processed plant or animal basic or raw materials (e.g. raw, baked, dried, fermented, smoked and/or boiled meat, bone, cartilage, fish, vegetables, fruit, herbs, nuts, vegetable or fruit juices or pastes or mixtures thereof), digestible or indigestible carbohydrates (e.g. sucrose, maltose, fructose, glucose, dextrins, amylose, amylopectin, inulin, xylan, cellulose, tagatose), sugar alcohols (e.g. sorbitol, erythritol), natural or hardened fats (e.g. tallow, lard, palm oil, coconut oil, hardened plant fat), oils (e.g. sunflower oil, peanut oil, corn oil, olive oil, fish oil, soybean oil, sesame oil), fatty acids or salts thereof (e.g. potassium stearate), proteinogenic or nonproteinogenic amino acids and related compounds (e.g. γ-aminobutyric acid, taurine), peptides (e.g. glutathione), native or processed proteins (e.g. gelatin), enzymes (e.g. peptidases), nucleic acids, nucleotides, other flavor correctants for unpleasant taste impressions, taste modulators for further, as a rule not unpleasant flavor impressions, flavor-modulating substances (e.g. inositol phosphate, nucleotides such as guanosine monophosphate, adenosine monophosphate or other substances such as sodium glutamates or 2-phenoxypropionic acid), emulsifiers (e.g. lecithins, diacylglycerols, gum arabic), stabilizers (e.g. carrageenan, alginate), preservatives (e.g. benzoic acid, sorbic acid), antioxidants (e.g. tocopherol, ascorbic acid), chelating agents (e.g. citric acid), organic or inorganic acidifying agents (e.g. malic acid, acetic acid, citric acid, tartaric acid, phosphoric acid), additional bitter substances (e.g. quinine, caffeine, limonin, amarogentin, humolones, lupolones, catechins, tannins), sweeteners (e.g. saccharin, cyclamate, aspartame, neotame), mineral salts (e.g. sodium chloride, potassium chloride, magnesium chloride, sodium phosphates), substances preventing enzymatic browning (e.g. sulfite, ascorbic acid), essential oils, plant extracts, natural or synthetic dyes or colored pigments (e.g. carotenoids, flavonoids, anthocyans, chlorophyll and derivatives thereof), spices, trigeminally effective substances or plant extracts containing said trigeminally effective substances, synthetic, natural or nature-identical aromatic substances or odoriferous substances and odor correctants.

Dental hygiene products according to the invention (as an example of preparations used for oral hygiene), which contain the compounds of formula (I) to be used according to the invention, salts or mixtures, generally comprise an abrasive system (abrasive or polishing agent), for example silicic acids, calcium carbonates, calcium phosphates, aluminum oxides and/or hydroxyapatites, surface-active substances e.g. sodium lauryl sulfate, sodium lauryl sarcosinate and/or cocamidopropyl betaine, humectants e.g. glycerol and/or sorbitol, thickening agents, e.g. carboxymethylcellulose, polyethylene glycols, carrageenan and/or Laponite®, sweeteners, e.g. saccharin, flavor correctants for unpleasant taste impressions, flavor correctants for further, as a rule not unpleasant taste impressions, taste-modulating substances (e.g. inositol phosphate, nucleotides such as guanosine monophosphate, adenosine monophosphate or other substances such as sodium glutamate or 2-phenoxypropionic acid), substances with a cooling effect e.g. menthol, menthol derivatives (e.g. L-menthol, L-menthyl lactate, L-menthyl alkyl carbonates, menthone ketals, menthane-carboxylic acid amides), 2,2,2-trialkyl acetic acid amides (e.g. 2,2-diisopropylpropionic acid methyl amide), icilin derivatives, stabilizers and active substances, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavoring materials and/or sodium bicarbonate or odor correctants.

As further constituents for (oral) pharmaceutical preparations according to the invention, it is possible to use all usual further active substances, base substances, excipients and additives for oral pharmaceutical preparations. As active substances it is in particular also possible to use unpleasant-tasting orally formulable active pharmaceutical ingredients. The active substances, base materials, excipients and additives can be transformed in a manner known per se into the oral dosage forms. This takes place regularly using inert, nontoxic, pharmaceutically suitable excipients. These include, among others, carriers (e.g. microcrystalline cellulose), solvents (e.g. liquid polyethylene glycols), emulsifiers (e.g. sodium dodecyl sulfate), dispersing agents (e.g. polyvinylpyrrolidone), synthetic and natural biopolymers (e.g. albumin), stabilizers (e.g. antioxidants such as ascorbic acid), colorants (e.g. inorganic pigments such as iron oxides) and odor correctants and other and/or flavor correctants not affecting the bitter taste.

Preferably, the preparations according to the invention can also contain one or a plurality of (further) odoriferous, aromatic and/or flavoring materials, to round off and improve the taste and/or odor of the preparation. Suitable flavoring compositions contain e.g. synthetic or natural aromas, odoriferous and/or flavoring materials and suitable auxiliaries and carriers. It is regarded as especially advantageous that any bitter or metallic taste impression that would stem from the aromatic or odoriferous substances contained in the preparations without the compounds of formula (I) to be used according to the invention, salts or mixtures (as defined above), can be altered and/or masked and therefore the overall aroma or taste profile is improved.

Preparations according to the invention that are in the form of semifinished products preferably contain additionally at least one further (synthetic or natural) aromatic substance, odoriferous substance and/or flavoring material and can serve for altering or masking the unpleasant taste impression of finished-product preparations that are produced using the semifinished-product preparation.

The invention also relates to a mixture, preferably a semifinished product for producing a preparation according to the invention as defined above, containing one, two or a plurality of different compounds of formula (I) as defined above, or
one, two or a plurality of different physiologically acceptable salts of one, two or a plurality of different compounds of formula (I) as defined above, or
a mixture of one, two or a plurality of different compounds of formula (I) as defined above with one, two or a plurality of different physiologically acceptable salts of one, two or a plurality of different compounds of formula (I) as defined above,
and
contains one, two, three, four, five, six, seven, eight, nine, ten or a plurality of further aromatic substances with a molar weight above 90 g/mol, preferably above 100 g/mol, preferably with a molar weight in the range from 110 g/mol through 300 g/mol, more preferably with a molar weight in the range from 120 g/mol through 250 g/mol, particularly preferably with a molar weight in the range from 125 g/mol through 220 g/mol, in particular preferably with a molar weight in the range from 130 g/mol through 210 g/mol, and preferably one or a plurality of carriers fit for consumption, preferably selected from the group consisting of ethanol, isopropanol, glycerol, 1,2-propylene glycol, diacetin, triacetin, maltodextrin, gum arabic, silicon dioxide and mixtures thereof.

The configurations described above, in particular the configurations characterized above as preferred or particularly preferred, with respect to the use according to the invention of the compounds of formulas (I), (I-A), (I-A1), (I-A2), (I-B), (II) and (II-A), apply correspondingly to a mixture according to the invention, in particular to a mixture that is preferred or particularly preferred according to the invention.

The configurations described above, in particular the configurations characterized above as preferred or particularly preferred, with respect to a preparation according to the invention, apply correspondingly to a mixture according to the invention, in particular to a preferred or particularly preferred mixture according to the invention.

A preferred mixture according to the invention contains one or a plurality of carriers fit for consumption selected from the group consisting of glycerol, 1,2-propylene glycol, diacetin, triacetin, maltodextrin, gum arabic, silicon dioxide and mixtures thereof.

A particularly preferred mixture according to the invention is characterized in that the mixture contains two, three, four, five, six, seven, eight, nine, ten or a plurality of further aromatic substances with a molar weight above 120 g/mol, preferably with a molar weight above 125 g/mol, preferably with a molar weight in the range from 125 g/mol through 220 g/mol, particularly preferably with a molar weight in the range from 130 g/mol through 210 g/mol.

A preferred mixture according to the invention preferably does not contain hexane and does not contain methylene chloride, and preferably does not contain hexane, methylene chloride, acetone or methanol.

A preferred mixture according to the invention is not a mixture that contains 4-dihydroxy-5,7-dihydroxy-4-(4-hydroxyphenyl)coumarin, α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5, bonaroside, helonioside A, helonioside B, lapathoside D, vanicoside B, vanicoside C, vanicoside F, asteryunnanoside, saikosaponin M, hydropiperoside, quercetin-3-O-β-D-glucuronide-6"-butyl ester and quercetin-3-O-β-D-glucuronide-6"-methyl ester.

Regarding the structural formulas corresponding to these compounds, reference is again made to the literature source Chin. J. Appl. Environ. Biol. 2009, 15, 615-620, which with respect to the corresponding compounds disclosed therein becomes part of this application by reference.

A preferred mixture according to the invention is not a mixture that contains 4-dihydroxy-5,7-dihydroxy-4-(4-hydroxyphenyl)coumarin, α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside in the proportions by weight of 4:9:8:37:30:24:14:5:12:41.

If a mixture according to the invention contains 4-dihydroxy-5,7-dihydroxy-4-(4-hydroxyphenyl)coumarin, one, a plurality of or all of the following conditions apply:

the weight ratio of 4-dihydroxy-5,7-dihydroxy-4-(4-hydroxyphenyl)coumarin to quercetin is not equal to 4:30,
the weight ratio of 4-dihydroxy-5,7-dihydroxy-4-(4-hydroxyphenyl)coumarin to cucurbitacin IIa is not equal to 4:24,
the weight ratio of 4-dihydroxy-5,7-dihydroxy-4-(4-hydroxyphenyl)coumarin to cucurbitacin U is not equal to 4:14,
the weight ratio of 4-dihydroxy-5,7-dihydroxy-4-(4-hydroxyphenyl)coumarin to 7'-dihydroxymatairesinol is not equal to 4:8, and wherein preferably at least one of the unpleasant, in particular bitter, tasting substances contained in the mixture is not quercetin, is not cucurbitacin IIa, is not cucurbitacin U and is not 7'-dihydroxymatairesinol.

If a mixture according to the invention contains 4-dihydroxy-5,7-dihydroxy-4-(4-hydroxyphenyl)coumarin, the ratio of the mass of 4-dihydroxy-5,7-dihydroxy-4-(4-hydroxyphenyl)coumarin to the total mass of α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside is not 4:180.

A preferred mixture according to the invention is not a mixture that contains α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5, bonaroside, helonioside A, helonioside B, lapathoside D, vanicoside B, vanicoside C, vanicoside F, asteryunnanoside, saikosaponin M, hydropiperoside, quercetin-3-O-β-D-glucuronide-6"-butyl ester and quercetin-3-O-β-D-glucuronide-6"-methyl ester.

A preferred mixture according to the invention is not a mixture that contains α-tocopherol quinone, (24S)-ethylcholesta-3β,5α,6α-triol, cucurbitacin IIa, cucurbitacin U, iotroridoside A, pokeweedcerebroside 5 and bonaroside.

A preferred mixture according to the invention does not contain any cucurbitacin IIa, preferably does not contain any cucurbitacin IIa and cucurbitacin U, and preferably does not contain any cucurbitacins.

A preferred mixture according to the invention is characterized in that the mixture does not contain one, two, three, four, five, six, seven, eight or all of the following substances: tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside, and/or the mixture does not contain any of the following substances: (24S)-ethylcholesta-3β,5α,6α-triol, iotroridoside A, pokeweedcerebroside 5, bonaroside, helonioside A, helonioside B, lapathoside D, vanicoside B, vanicoside C, vanicoside F, asteryunnanoside, hydropiperoside.

Mixtures according to the invention that are in the form of semifinished products or aroma and/or flavoring compositions and so are not suitable for direct consumption, and that can be used for producing a preparation according to the invention suitable for direct consumption, preferably contain a total amount of compounds of formula (I) as defined above and of physiologically acceptable salts of the compounds of formula (I) as defined above in the range from 0.001 wt % through 95 wt %, preferably in the range from 0.005 through 80 wt %, particularly preferably in the range from 0.01 wt % through 50 wt %, more preferably in the range from 0.05 wt % through 40 wt %, in each case relative to the total weight of the mixture.

Preparations to be used according to the invention that are in the form of semifinished products can serve for altering or masking the unpleasant flavor impression of finished-product preparations that are produced using the semifinished-product preparation.

In a particularly preferred embodiment of the invention, the compounds of formula (I) to be used according to the invention, salts or mixtures are used in the preparations according to the invention in combination with at least one further substance for altering or masking the unpleasant flavor impression of an unpleasant-tasting substance. Particularly effective masking can be achieved in this way. In particular the combination of the compounds of formula (I) to be used according to the invention, salts or mixtures with other flavor correctants for unpleasant, in particular bitter flavor impressions is preferred.

Further substances for altering or masking an unpleasant taste impression and/or for intensifying a pleasant taste impression or flavor correctants are preferably selected from the group consisting of nucleotides (e.g. adenosine-5'-monophosphate, cytidine-5'-monophosphate) or physiologically acceptable salts thereof, lactisoles, sodium salts (e.g. sodium chloride, sodium lactate, sodium citrate, sodium acetate, sodium gluconoate), hydroxyflavanones, here preferably eriodictyol, sterubin (eriodictyol-7-methyl ether), homoeriodictyol, and sodium, potassium, calcium, magnesium or zinc salts thereof (in particular as described in EP 1 258 200 A2, which with respect to the corresponding compounds disclosed therein forms part of this application by reference), hydroxybenzoic acid amides, here preferably 2,4-dihydroxybenzoic acid vanillyl amide, 2,4-dihydroxybenzoic acid-N-(4-hydroxy-3-methoxybenzyl)amide, 2,4,6-trihydroxybenzoic acid-N-(4-hydroxy-3-methoxybenzyl)amide, 2-hydroxybenzoic acid-N-4-(hydroxy-3-methoxybenzyl) amide, 4-hydroxybenzoic acid-N-(4-hydroxy-3-methoxybenzyl)amide, 2,4-dihydroxybenzoic acid-N-(4-hydroxy-3-methoxybenzyl)amide-monosodium salt, 2,4-dihydroxybenzoic acid-N-2-(4-hydroxy-3-methoxyphenyl) ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide; 4-hydroxybenzoic acid vanillyl amides (in particular as described in WO 2006/024587, which with respect to the corresponding compounds disclosed therein forms part of this application by reference); hydroxydeoxybenzoins, here preferably 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone and 1-(2-hydroxy-4-methoxyphenyl)-2-(4-hydroxy-3-methoxyphenyl)ethanone) (in particular as described in WO 2006/106023, which with respect to the corresponding compounds disclosed therein forms part of this application by reference); hydroxyphenylalkane diones, such as for example gingerdione-[2], gingerdione-[3], gingerdione-[4], dehydrogingerdione-[2], dehydrogingerdione-[3], dehydrogingerdione-[4]) (in particular as described in WO 2007/003527, which with respect to the corresponding compounds disclosed therein forms part of this application by reference); diacetyl trimers (in particular as described in WO 2006/058893, which with respect to the corresponding compounds disclosed therein forms part of this application by reference); gamma-aminobutyric acids (in particular as described in WO 2005/096841, which with respect to the corresponding compounds disclosed therein forms part of this application by reference); divanillins (in particular as described in WO 2004/078302, which with respect to the corresponding compounds disclosed therein forms part of this application by reference) and 4-hydroxydihydrochalcones (preferably as described in US 2008/0227867 A1, which with respect to the corresponding compounds disclosed therein forms part of this application by reference), and in particular phloretin and davidigenin, amino acids or mixtures of whey proteins with lecithins, hesperetin as disclosed in WO 2007/014879, which with respect to these compounds becomes part of this application by reference, 4-hydroxydihydrochalcones as disclosed in WO 2007/107596, which with respect to these compounds becomes part of this application by reference, or propenylphenyl glycosides (chavicol glycosides) as described in EP 1 955 601 A1, which with respect to these compounds becomes part of this application by reference, or extracts of *Rubus suavissimus* as described in the European patent application with the application number 11 165 566.8 (Symrise), which with respect to these extracts becomes part of this application by reference, or extracts of *Hydrangea macrophylla* as described in EP 2 298 084 A1, which with respect to these extracts becomes part of this application by reference, pellitorin and derived aroma compositions as described in EP 2 008 530 A1, which with respect to these aroma compositions becomes part of this application by reference, umami compounds as described in WO 2008/046895 A1 and EP 1 989 944 A1, which in each case with respect to these compounds form part of this application by reference, umami compounds as described in EP 2 064 959 A1 or EP 2 135 516 A1, which with respect to the corresponding compounds disclosed therein form part of this application by reference and vanillyl lignans as described in the European patent application with the application number 11 164 373.0 (Symrise), which forms part of this application by reference.

The invention further relates to a method for (a) altering or masking the unpleasant, in particular bitter, taste impression of one, two or a plurality of unpleasant, in particular bitter, tasting substances and/or (b) producing a preparation according to the invention as defined above, with the following step:

contacting or mixing the unpleasant, in particular bitter, tasting substance or substances with one, two or a plurality of different compounds of formula (I) as defined above, or
one, two or a plurality of different physiologically acceptable salts of one, two or a plurality of different compounds of formula (I) as defined above,
or
a mixture of one, two or a plurality of different compounds of formula (I) as defined above with one, two or a plurality of different physiologically acceptable salts of one, two or a plurality of different compounds of formula (I) as defined above.

EXAMPLES

The examples serve for clarifying the invention, without limiting it. Unless stated otherwise, all data refer to weight.
Standard Operating Procedure (SOP 1)
A suspension of 20 mmol of the corresponding cinnamic acid derivatives, 30 mmol phloroglucinol, 12 g montmorillonite K-10 in 100 ml of 1,4-dioxane is refluxed for 24 hours. Then the catalyst is filtered off and the filter residue is washed with THF. The combined filtrates are evaporated to dryness in a rotary evaporator. The concentrated filtrate is dissolved in 250 ml ethyl acetate and washed with 100 ml of 5% sodium bicarbonate solution and 100 ml of saturated sodium chloride solution. The organic phase is dried over sodium sulfate and the solvent is removed in a rotary evaporator. The solid thus obtained is then recrystallized from 200 through 350 ml of water.

Example 1

(4S)-5,7-Dihydroxy-4-(2-hydroxyphenyl)chroman-2-one (1) and (4R)-5,7-dihydroxy-4-(2-hydroxyphenyl)chroman-2-one (2)

50 mmol phloroglucin and 25 mmol o-hydroxycinnamic acid were put in 75 ml of 1,4-dioxane and 1.0 ml concentrated sulfuric acid and heated under reflux for 12 hours. The reaction mixture was poured into 300 ml water and extracted with 250 ml ethyl acetate. The combined organic phases were then washed 5× with 100 ml of water and 2× with 100 ml of 5% sodium bicarbonate solution, dried and concentrated by evaporation. The solid obtained was recrystallized from hexane/acetone (2:1).
Yield: 4.7 mmol (19% of theor.)

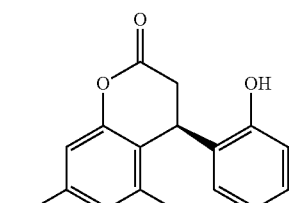

(1)

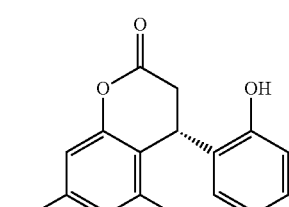

(2)

Analysis Data:
$^1$H-NMR (400 MHz, (CD$_3$)$_2$SO): 2.81 (dd, J=1.6/15.8 Hz, 1H); 3.06 (dd, J=7.4/15.8 Hz, 1H); 4.60 (d, J=7.1 Hz, 1H); 6.03 (d, J=2.3 Hz 1H); 6.16 (d, J=2.3 Hz, 1H); 6.46 (dd, J=1.7/7.6 Hz, 1H); 6.61 (dt, J=1.2/7.5 Hz, 1H); 6.81 (dd, J=1.1/8.0 Hz, 1H); 7.02 (dt, 1.7/7.6 Hz, 1H); 9.52 (bs, 1H); 9.66 (bs, 2H) ppm.
$^{13}$C-NMR (100 MHz, (CD$_3$)$_2$SO): 28.9 (CH); 35.2 (CH$_2$); 94.4 (CH); 98.6 (CH); 102.2 (C); 115.0 (CH); 118.7 (CH); 126.8 (CH); 127.7 (CH); 127.8 (C); 153.5 (C); 154.6 (C); 155.2 (C); 157.7 (C); 167.9 (C=O) ppm.
HRMS [M-H; C$_{15}$H$_{11}$O$_5$]: calc.: 271.0612. found: 271.0655.

Example 2

(4S)-5,7-Dihydroxy-4-(3-hydroxy-4-methoxyphenyl)chroman-2-one (3) and (4R)-5,7-dihydroxy-4-(3-hydroxy-4-methoxyphenyl)chroman-2-one (4)

Phloroglycinol and isoferulic acid were reacted together according to SOP1.

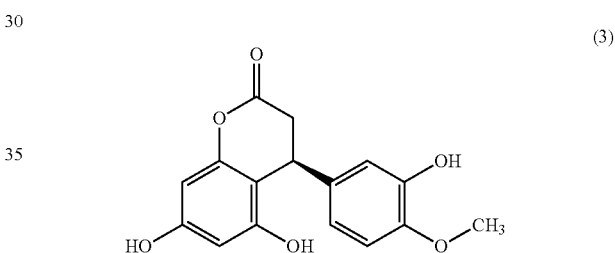

(3)

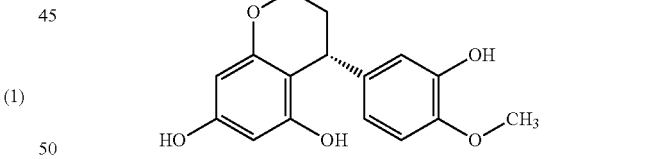

(4)

Yield: 1.1 mmol (6% of theor.)
Analysis Data:
$^1$H-NMR (400 MHz, CD$_3$OD): 2.90 (dd, J=1.9/15.7 Hz, 1H); 3.02 (dd, J=6.9/15.7 Hz, 1H); 3.78 (s, 3H); 4.43 (dd, J=1.9/6.9 Hz, 1H); 6.08 (dd, J=0.4/2.3 Hz 1H); 6.16 (d, J=2.3 Hz, 1H); 6.54 (ddd, J=0.7/2.3/8.3 Hz, 1H); 6.58 (d, J=2.2 Hz, 1H); 6.79 (d, J=8.3 Hz, 1H) ppm.
$^{13}$C-NMR (100 MHz, CD$_3$OD): 35.2 (CH); 38.6 (CH$_2$); 56.4 (CH$_3$); 96.1 (CH); 99.9 (CH); 105.4 (C); 112.9 (CH); 115.1 (CH); 119.0 (CH); 136.4 (C); 147.6 (C); 147.9 (C); 154.6 (C); 156.9 (C); 159.3 (C); 170.6 (C=O) ppm.
Mass spectrum (EI): (%)=303 (20); 302 (M$^{\cdot+}$, 100); 259 (34); 243 (30); 229 (19); 179 (16); 176 (39); 124 (52); 69 (24); 28 (17).

Example 3

(4S)-5,7-Dihydroxy-4-(4-hydroxy-3-methoxyphenyl)chroman-2-one (5) and (4R)-5,7-dihydroxy-4-(4-hydroxy-3-methoxyphenyl)chroman-2-one (6)

Phloroglycinol and ferulic acid were reacted together according to SOP1.

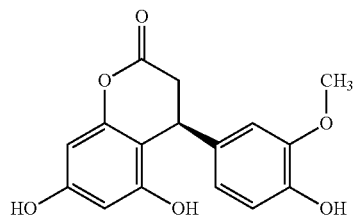
(5)

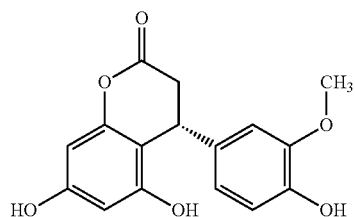
(6)

Yield: 4.8 mmol (24% of theor.)

Analysis Data:

$^1$H-NMR (400 MHz, CD$_3$OD): 2.90 (dd, J=2.0/15.7 Hz, 1H); 3.02 (dd, J=6.8/15.7 Hz, 1H); 3.76 (s, 3H); 4.47 (dd, J=2.0/6.8 Hz, 1H); 6.09 (dd, J=0.4/2.3 Hz 1H); 6.17 (d, J=2.3 Hz, 1H); 6.61 (ddd, J=0.7/2.1/8.2 Hz, 1H); 6.67 (d, J=8.2 Hz, 1H); 6.73 (d, J=2.1 Hz, 1H) ppm.

$^{13}$C-NMR (100 MHz, CD$_3$OD): 35.2 (CH); 38.6 (CH$_2$); 56.2 (CH$_3$); 96.1 (CH); 99.9 (CH); 105.5 (C); 111.7 (CH); 116.2 (CH); 120.1 (CH); 135.1 (C); 146.4 (C); 149.0 (C); 154.6 (C); 156.9 (C); 159.3 (C); 170.7 (C=O) ppm.

Mass spectrum (EI): (%)=303 (18); 302 (M$^{I+}$, 100); 259 (49); 244 (15); 243 (32); 229 (31); 179 (25); 176 (28); 124 (88); 77 (13).

Example 4

(4S)-5,7-Dihydroxy-4-(4-hydroxyphenyl)chroman-2-one (7) and (4R)-5,7-dihydroxy-4-(4-hydroxyphenyl)chroman-2-one (8)

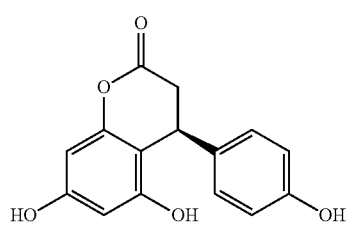
(7)

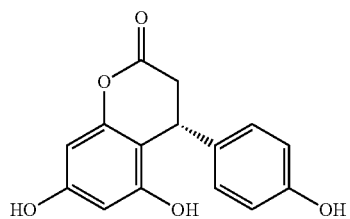
(8)

1.190 mol phloroglycine and 0.912 mol trans-4-hydroxycinnamic acid were put in 850 ml 1,4-dioxane and 0.187 mol concentrated sulfuric acid was added. The reaction mixture was heated under reflux for 16 hours. After cooling, the reaction mixture was poured into 4 l distilled water and left to stand overnight at room temperature. The precipitated crude product was filtered off and washed with ice water. After recrystallizing from 1.4 l water and 0.4 l ethanol, the residual solvent was removed from the product in a vacuum drying cabinet at 70° C.

Yield: 0.273 mol (30% of theor.)

Analysis Data:

$^1$H-NMR (400 MHz, (CD$_3$)$_2$SO): 2.76 (dd, J=1.8/15.8 Hz, 1H); 3.12 (dd, J=7.0/15.8 Hz, 1H); 4.32 (dd, J=1.2/6.7 Hz, 1H); 6.01 (d, J=2.2 Hz, 1H); 6.16 (d, J=2.3 Hz, 1H); 6.65 (m, 2H); 6.85 (m, 2H); 9.26 (bs, 1H); 9.53 (bs, 1H); 9.69 (bs, 1H) ppm.

$^{13}$C-NMR (100 MHz, (CD$_3$)$_2$SO): 32.8 (CH); 37.3 (CH$_2$); 94.5 (CH); 98.6 (CH); 103.5 (C); 115.1 (CH); 127.5 (CH); 132.4 (C); 152.8 (C); 155.2 (C); 155.9 (C); 157.6 (C); 167.9 (C=O) ppm.

Mass spectrum (EI): (%)=273 (13); 272 (M$^{I+}$, 77); 244 (12); 230 (16); 229 (100); 213 (39); 179 (39); 178 (25); 150 (19); 69 (27).

Example 5

(4S)-5,7-Dihydroxy-4-(4-methoxyphenyl)chroman-2-one (9) and (4R)-5,7-dihydroxy-4-(4-methoxyphenyl)chroman-2-one (10)

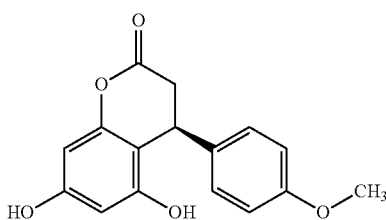
(9)

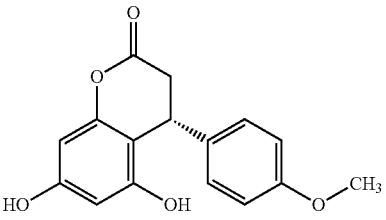
(10)

Phloroglycinol and trans-4-methoxycinnamic acid were reacted together according to SOP1.

Yield: 2.6 mmol (13% of theor.)

Analysis Data:

$^1$H-NMR (400 MHz, CD$_3$OD): 2.87 (dd, J=1.9/15.7 Hz, 1H); 3.03 (dd, J=6.9/15.7 Hz, 1H); 3.74 (s, 3H); 4.49 (dd, J=1.9/6.9 Hz, 1H); 6.09 (dd, J=0.4/2.3 Hz 1H); 6.16 (d, J=2.3 Hz, 1H); 6.80 (m, 2H); 6.01 (m, 2H) ppm.

$^{13}$C-NMR (100 MHz, CD$_3$OD): 34.9 (CH); 38.6 (CH$_2$); 55.7 (CH$_3$); 96.1 (CH); 99.9 (CH); 105.4 (C); 115.0 (CH); 128.9 (CH); 135.5 (C); 154.6 (C); 156.9 (C); 159.4 (C); 160.0 (C); 170.5 (C=O) ppm.

Mass spectrum (EI): m/z (%)=287 (12); 286 (M$^{\prime+}$, 68); 243 (54); 229 (11); 213 (37); 178 (22); 150 (16); 108 (100); 77 (10); 69 (20).

Example 6

(4S)-4-(1,3-Benzodioxol-5-yl)-5,7-dihydroxy-chroman-2-one (11) and (4R)-4-(1,3-benzodioxol-5-yl)-5,7-dihydroxy-chroman-2-one (12)

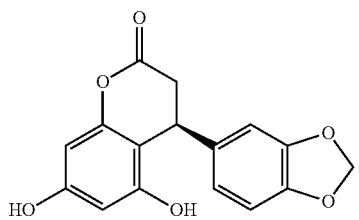

(11)

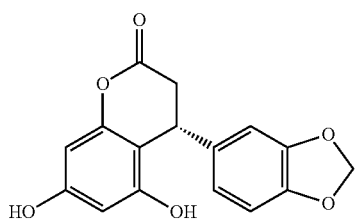

(12)

Phloroglycinol and trans-(3,4-methylene dioxy)cinnamic acid were reacted together according to SOP1.

Yield: 0.8 mmol (4% of theor.)

Analysis Data:

$^1$H-NMR (400 MHz, (CD$_3$)$_2$SO): 2.80 (dd, J=1.9/16.0 Hz, 1H); 3.15 (dd, J=7.0/15.8 Hz, 1H); 4.36 (d, J=7.0 Hz, 1H); 5.96 (s, 2H); 6.01 (d, J=2.3 Hz, 1H); 6.17 (d, J=2.3 Hz, 1H); 6.45 (ddd, J=0.6/1.9/8.0 Hz, 1H); 6.67 (d, J=1.8 Hz, 1H); 6.79 (d, J=8.0 Hz, 1H); 9.57 (bs, 1H); 9.76 (bs, 1H) ppm.

$^{13}$C-NMR (100 MHz, (CD$_3$)$_2$SO): 33.3 (CH); 37.1 (CH$_2$); 94.6 (CH); 98.6 (CH); 100.8 (CH$_2$); 103.1 (C); 107.2 (CH); 108.1 (CH); 119.2 (CH); 136.2 (C); 145.8 (C); 147.3 (C); 152.8 (C); 155.2 (C); 157.8 (C); 167.7 (C=O) ppm.

Mass spectrum (EI): (%)=301 (18); 300 (M$^{\prime+}$, 100); 258 (13); 257 (74); 174 (37); 122 (64); 115 (13); 69 (24); 63 (12); 28 (20).

Example 7

(4S)-4-(3,4-Dimethoxyphenyl)-5,7-dihydroxy-chroman-2-one (13) and (4R)-4-(3,4-dimethoxyphenyl)-5,7-dihydroxy-chroman-2-one (14)

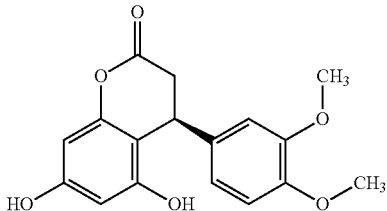

(13)

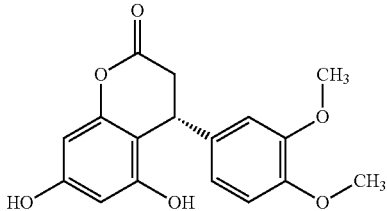

(14)

Phloroglycinol and trans-3,4-dimethoxycinnamic acid were reacted together according to SOP1.

Yield: 3.6 mmol (18% of theor.)

Analysis Data:

$^1$H-NMR (400 MHz, CD$_3$OD): 2.91 (dd, J=2.0/15.7 Hz, 1H); 3.05 (dd, J=6.9/15.7 Hz, 1H); 3.75 (s, 3H); 3.77 (s, 3H); 4.50 (dd, J=1.8/6.8 Hz, 1H); 6.08 (dd, J=0.4/2.2 Hz 1H); 6.17 (d, J=2.2 Hz, 1H); 6.61 (ddd, J=0.7/2.2/8.3 Hz, 1H); 6.79 (d, J=2.2 Hz, 1H); 6.82 (d, J=8.3 Hz, 1H) ppm.

$^{13}$C-NMR (100 MHz, CD$_3$OD): 35.3 (CH); 38.5 (CH$_2$); 56.4 (CH$_3$); 56.5 (CH$_3$); 96.2 (CH); 100.0 (CH); 105.4 (C); 112.2 (CH); 113.1 (CH); 120.0 (CH); 136.6 (C); 149.4 (C); 150.6 (C); 154.7 (C); 157.0 (C); 159.5 (C); 170.6 (C=O) ppm.

Mass spectrum (EI): m/z (%)=317 (16); 316 (M$^{\prime+}$, 85); 273 (29); 259 (15); 243 (47); 190 (23); 139 (12); 138 (100); 77 (13); 69 (22).

Example 8

(4S)-4-(3,4-Dihydroxyphenyl)-5,7-dihydroxy-chroman-2-one (15) and (4R)-4-(3,4-dihydroxyphenyl)-5,7-dihydroxy-chroman-2-one (16)

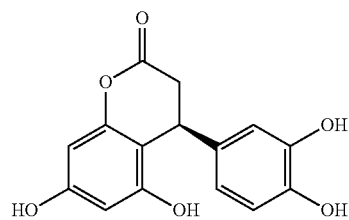

(15)

-continued

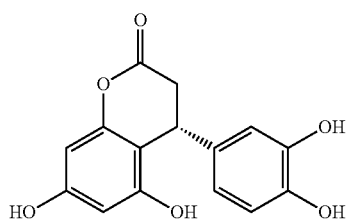
(16)

A suspension of 40.0 mmol phloroglycine, 35.0 mmol trans-3,4-dihydroxycinnamic acid and 16.0 g montmorillonite in 150 ml 1,4-dioxane was heated under reflux for 24 hours. Then the catalyst was filtered off and the filter residue was washed with THF. The combined organic phases were then concentrated by evaporation and the residue was purified by silica-gel chromatography (solvent: ethyl acetate/hexane 3:2). Then it was recrystallized from 100 ml demineralized water.

Yield: 7.3 mmol (21% of theor.)

Analysis Data:

$^1$H-NMR (400 MHz, $(CD_3)_2SO$): 2.72 (dd, J=1.8/15.8 Hz; 1H); 3.09 (dd, J=7.0/15.8 Hz; 1H); 4.25 (d, J=6.8 Hz, 1H); 6.00 (d, J=2.2 Hz, 1H); 6.15 (d, J=8.3 Hz, 1H); 6.34 (dd, J=2.3/8.1 Hz; 1H); 6.42 (d, J=2.2 Hz, 1H); 6.60 (d, J=8.1 Hz, 1); 8.82 (bs, 2H); 9.63 (bs, 2H) ppm.

$^{13}$C-NMR (100 MHz, $(CD_3)_2SO$): 33.0 (CH); 37.4 ($CH_2$); 94.5 (CH); 98.6 (CH); 103.6 (C); 114.0 (CH); 115.5 (CH); 117.3 (CH); 133.2 (C); 143.8 (C); 145.0 (C); 152.8 (C); 155.2 (C); 157.6 (C); 167.9 (C=O) ppm.

HRMS [M-H; $C_{15}H_{11}O_6$]: calc.: 287.0561. found: 287.0622.

Example 9

(4S)-7-Hydroxy-4-(4-hydroxyphenyl)chroman-2-one (17) and (4R)-7-hydroxy-4-(4-hydroxyphenyl)chroman-2-one (18)

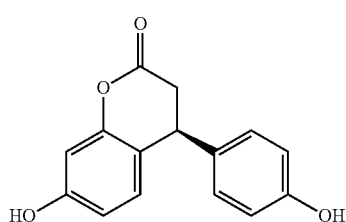
(17)

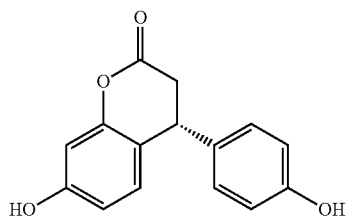
(18)

0.5 g para-toluenesulfonic acid and 1.5 ml concentrated sulfuric acid were added to a mixture of 55 mmol trans-4-hydroxycinnamic acid and 50 mmol resorcinol in 75 ml of 1,4-dioxane and heated under reflux for 12 hours. Then a large part of the solvent was removed in a rotary evaporator and the product mixture was taken up in 200 ml ethyl acetate. The organic phase was washed twice with 50 ml of demineralized water and 5% sodium bicarbonate solution and once with saturated sodium chloride solution. After removing the solvent, the product was purified by silica-gel column chromatography (solvent: ethyl acetate/hexane 1:1), it was recrystallized from a solvent mixture of diethyl ether/pentane (4:15) and the product was dried in a vacuum drying cabinet at 60° C.

Yield: 9.7 mmol (19% of theor.)

Analysis Data:

$^1$H-NMR (400 MHz, $(CD_3)_2SO$): 2.94 (dd, J=6.5/15.8 Hz, 1H); 3.05 (dd, J=6.0/15.8 Hz, 1H); 4.24 (t, J=6.1 Hz, 1H); 6.51 (d, J=2.3 Hz, 1H); 6.54 (dd, J=2.4/8.2 Hz, 1H); 6.71 (m, 2H); 6.84 (m, 1H); 6.92 (m, 2H) ppm.

$^{13}$C-NMR (100 MHz, $(CD_3)_2SO$): 36.9 ($CH_2$); 37.9 (CH); 103.2 (CH); 111.5 (CH); 115.4 (CH); 116.7 (C); 128.1 (CH); 128.8 (CH); 131.8 (C); 151.8 (C); 156.2 (C); 157.4 (C); 167.8 (C=O) ppm.

Mass spectrum (EI): (%)=256 ($M^{'+}$, 76); 228 (26); 214 (20); 213 (100); 197 (42); 115 (15); 77 (21); 65 (17); 51 (15); 39 (21).

Example 10

(4S)-5-Hydroxy-4-(4-hydroxy-3-methoxyphenyl)-7-methoxy-chroman-2-one (19) and (4R)-5-hydroxy-4-(4-hydroxy-3-methoxyphenyl)-7-methoxy-chroman-2-one (20) and (4S)-7-hydroxy-4-(4-hydroxy-3-methoxyphenyl)-5-methoxy-chroman-2-one (21) and (4R)-7-hydroxy-4-(4-hydroxy-3-methoxyphenyl)-5-methoxy-chroman-2-one (22)

0.5 ml concentrated sulfuric acid was added to a mixture of 17.5 mmol trans-4-hydroxycinnamic acid and 17.5 mmol 5-methylresorcinol in 40 ml 1,4-dioxane and heated under reflux for 12 hours. After cooling, the reaction mixture was poured into 250 ml demineralized water and extracted with 150 ml ethyl acetate (EAc). The organic phase was washed twice, each time with 50 ml demineralized water and 50 ml 5% sodium bicarbonate solution, and was dried over sodium sulfate. After removing the solvent, the product was purified by silica-gel column chromatography (solvent: ethyl acetate/hexane 2:3). According to NMR, the product consisted of two isomers, which were present in the ratio 37:63 (19/20:21/22). Further separation was carried out by preparative HPLC (Phenomenex Luna C18 (2), 5 µm, 150×21.5 mm; acetonitrile/water 75:25; 25 ml/min; 105 bar)

Yield: 9.8 mmol (56% of theor.)

Example 10a (4S)-5-Hydroxy-4-(4-hydroxy-3-methoxyphenyl)-7-methoxy-chroman-2-one (19) and (4R)-5-hydroxy-4-(4-hydroxy-3-methoxyphenyl)-7-methoxy-chroman-2-one (20)

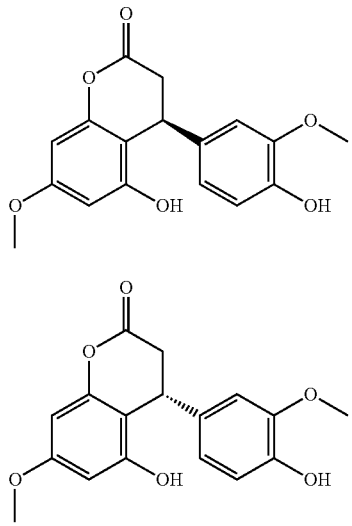

(19)

(20)

Analysis Data:

Retention time: 20.3 min-21.8 min $^1$H-NMR (400 MHz, CDCl$_3$): 2.97 (dd, J=3.6/15.8 Hz; 1H); 3.03 (dd, J=6.1/15.8 Hz; 1H); 3.79 (s, 3H); 3.82 (s, 3H); 4.44 (dd, J=3.6/6.1 Hz, 1H); 4.96 (bs, 1H); 5.53 (bs, 1H); 6.21 (d, J=2.3 Hz, 1H); 6.35 (d, J=2.3 Hz, 1H); 6.62 (d, J=2.0 Hz; 1H); 6.64 (dd, J=2.0/8.6 Hz, 1H); 6.82 (d, J=8.6 Hz, 1H) ppm.

$^{13}$C-NMR (100 MHz, (CD$_3$)$_2$SO): 33.2 (CH); 37.1 (CH$_2$); 55.1 (CH$_3$); 55.5 (CH$_3$); 93.0 (CH); 97.5 (CH); 105.2 (C); 111.3 (CH); 115.2 (CH); 118.2 (CH); 132.7 (C); 145.3 (C); 147.5 (C); 154.0 (C); 155.3 (C); 159.5 (C); 167.8 (C=O) ppm.

HRMS [M-H; C$_{17}$H$_{15}$O$_6$]: calc.: 315.0874. found: 315.0902.

Example 10b (4S)-7-Hydroxy-4-(4-hydroxy-3-methoxyphenyl)-5-methoxy-chroman-2-one (21) and (4R)-7-hydroxy-4-(4-hydroxy-3-methoxyphenyl)-5-methoxy-chroman-2-one (22)

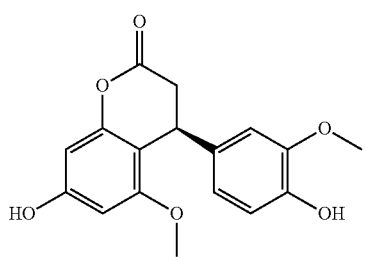

(21)

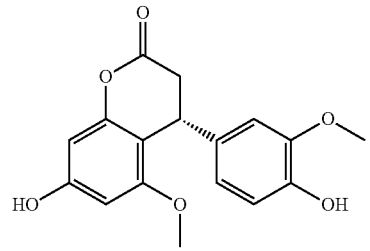

(22)

Analysis Data:

Retention time: 17.0 min-19.8 min $^1$H-NMR (400 MHz, CDCl$_3$): 2.95-2.99 (KB, 2H); 3.76 (s, 3H); 3.81 (s, 3H); 4.48 (dd, J=3.9/4.7 Hz, 1H); 5.19 (bs, 1H); 5.49 (bs, 1H); 6.25 (d, J=2.3 Hz, 1H); 6.27 (d, J=2.3 Hz, 1H); 6.59 (dd, J=2.1/7.9 Hz; 1H); 6.61 (d, J=2.1 Hz, 1H); 6.79 (d, J=7.9 Hz, 1H) ppm.

$^{13}$C-NMR (100 MHz, (CD$_3$)$_2$SO): 33.1 (CH); 38.8-40.1 (CH$_2$; masked by solvent signal); 55.5 (CH$_3$); 55.6 (CH$_3$); 95.4 (CH); 95.6 (CH); 104.3 (C); 111.1 (CH); 115.2 (CH); 118.1 (CH); 132.7 (C); 145.3 (C); 147.5 (C); 152.5 (C); 157.0 (C); 158.2 (C); 167.7 (C=O) ppm.

HRMS [M-H; Cl$_7$H$_{15}$O$_6$]: calc.: 315.0874. found: 315.0920.

Example 11

(4S)-7-Hydroxy-4-(4-hydroxy-3-methoxyphenyl)chroman-2-one (23) and (4R)-7-hydroxy-4-(4-hydroxy-3-methoxyphenyl)chroman-2-one (24)

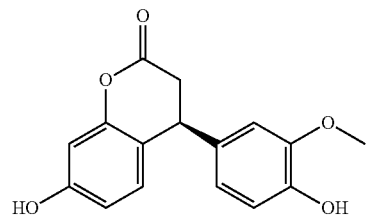

(23)

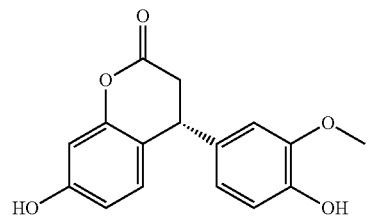

(24)

5 mmol p-toluenesulfonic acid was added to a mixture of 100 mmol ferulic acid and 120 mmol resorcinol in 150 ml 1,4-dioxane and heated under reflux for 14 hours. Then the reaction mixture was evaporated to dryness and was recrystallized from a mixture consisting of 450 ml water and 150 ml ethanol. The crystallized product was dissolved in 250 ml ethyl acetate, the organic phase was washed twice with 150 ml 5% sodium bicarbonate solution each time and once with 100 ml of saturated sodium chloride solution and dried over sodium sulfate. After removing the solvent, the product was dried at 60° C. in a vacuum drying cabinet.

Yield: 22.6 mmol (23% of theor.)

Analysis Data:

$^1$H-NMR (400 MHz, $(CD_3)_2SO$): 3.00 (dd, J=6.6/15.9 Hz, 1H); 3.05 (dd, J=6.1/15.8 Hz, 1H); 3.72 (s, 3H); 4.24 (t, J=6.3 Hz, 1H); 6.45 (dd, J=2.1/8.1 Hz, 1H); 6.51 (d, J=2.3 Hz, 1H); 6.54 (dd, J=2.4/8.2 Hz, 1H); 6.70 (d, J=8.1 Hz, 1H); 6.78 (d, J=2.1 Hz, 1H), 6.84 (d, J=8.3 Hz, 1H); 8.97 (bs, 1H); 9.68 (bs, 1H) ppm.

$^{13}$C-NMR (100 MHz, $(CD_3)_2SO$): 36.8 ($CH_2$); 38.3 (CH); 55.5 ($CH_3$); 103.1 (CH); 111.5 (CH); 111.6 (CH); 115.4 (CH); 116.6 (C); 119.3 (CH); 128.8 (CH); 132.4 (C); 145.5 (C); 147.6 (C); 151.8 (C); 157.4 (C); 167.9 (C=O) ppm.

Mass spectrum (EI): (%)=287 (18); 286 (M$^+$, 100); 253 (14); 243 (51); 228 (17); 227 (36); 213 (39); 176 (18); 115 (17); 77 (15).

Example 12

(4S)-7-Hydroxy-4-(3-hydroxy-4-methoxyphenyl) chroman-2-one (25) and (4R)-7-hydroxy-4-(3-hydroxy-4-methoxyphenyl) chroman-2-one (26)

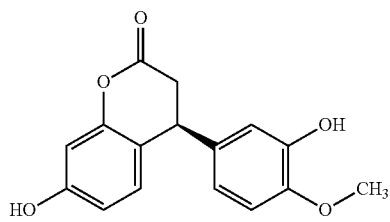
(25)

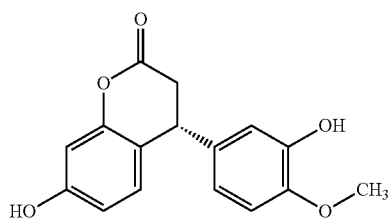
(26)

0.5 g para-toluenesulfonic acid and 1.5 ml concentrated sulfuric acid were added to a mixture of 50 mmol isoferulic acid and 75 mmol resorcinol in 75 ml of 1,4-dioxane and heated under reflux for 14 hours. As the reaction was not completed at this time point according to LC-MS, a further 1.5 ml of concentrated sulfuric acid was added and the mixture was heated for a further 10 hours. Then a large part of the solvent was removed in a rotary evaporator and the product mixture was taken up in 200 ml ethyl acetate. The organic phase was washed twice with 50 ml demineralized water and 5% sodium bicarbonate solution each time and once with saturated sodium chloride solution. The organic phase was then dried over sodium sulfate and after removing the solvent, the product was purified by silica-gel column chromatography (solvent: ethyl acetate/hexane 4:5), recrystallized from a solvent mixture of diethyl ether/pentane (1:6) and the resultant product was dried at 60° C. in a vacuum drying cabinet.

Yield: 21.6 mmol (43% of theor.)

Analysis Data:

$^1$H-NMR (400 MHz, $(CD_3)_2SO$): 2.90 (dd, J=5.9/15.8 Hz, 1H); 3.07 (dd, J=6.1/15.8 Hz, 1H); 3.72 (s, 3H); 4.21 (t, J=5.9 Hz, 1H); 6.50-6.53 (KB, 3H); 6.54 (dd, J=2.4/8.2 Hz, 1H); 6.84 (d, J=8.4 Hz, 1H); 6.87 (d, J=8.2 Hz, 1H); 9.02 (bs, 1H); 9.68 (bs, 1H) ppm.

$^{13}$C-NMR (100 MHz, $(CD_3)_2SO$): 36.9 ($CH_2$); 38.1 (CH); 55.5 ($CH_3$); 103.2 (CH); 111.6 (CH); 112.4 (CH); 114.3 (CH); 116.4 (C); 117.7 (CH); 129.0 (CH); 134.4 (C); 146.5 (C); 146.6 (C); 151.8 (C); 157.4 (C); 167.7 (C=O) ppm.

Mass spectrum (EI): mk (%)=287 (19); 286 (M'$^+$, 100); 253 (21); 243 (42); 229 (21); 227 (41); 213 (25); 176 (24); 115 (21); 77 (20).

Example 13

(4S)-4-(3,4-Dihydroxyphenyl)-7-hydroxy-chroman-2-one (27) and (4R)-4-(3,4-dihydroxyphenyl)-7-hydroxy-chroman-2-one (28)

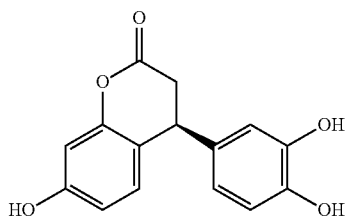
(27)

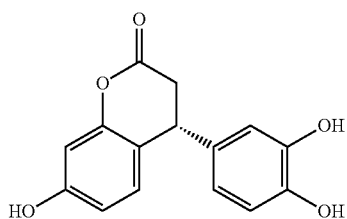
(28)

0.5 g para-toluenesulfonic acid and 1.5 ml concentrated sulfuric acid were added to a mixture of 55 mmol caffeic acid and 50 mmol resorcinol in 75 ml of 1,4-dioxane and heated under reflux for 12 hours. Then a large part of the solvent was removed in a rotary evaporator and the product mixture was taken up in 200 ml ethyl acetate. The organic phase was washed twice with 50 ml demineralized water and 5% sodium bicarbonate solution each time and once with saturated sodium chloride solution. The organic phase was dried over sodium sulfate and, after removing the solvent, the product was purified by silica-gel column chromatography (solvent: ethyl acetate/hexane 1:1), recrystallized from a solvent mixture of diethyl ether/pentane (1:6) and the resultant product was dried at 60° C. in a vacuum drying cabinet.

Yield: 9.9 mmol (20% of theor.)

Analysis Data:

$^1$H-NMR (400 MHz, $(CD_3)_2SO$): 2.87 (dd, J=5.8/15.8 Hz, 1H); 3.05 (dd, J=6.1/15.8 Hz, 1H); 4.16 (t, J=5.9 Hz, 1H); 6.39 (ddd, J=0.5/2.2/8.0 Hz, 1H); 6.47 (dd, J=0.3/2.2 Hz, 1H); 6.50 (d, J=2.4 Hz, 1H); 6.54 (dd, J=2.4/8.3 Hz, 1H); 6.66 (d, J=8.0 Hz, 1H), 6.87 (dd, J=0.7/8.3 Hz, 1H); 9.11 (bs, 3H) ppm.

$^{13}$C-NMR (100 MHz, $(CD_3)_2SO$): 37.0 ($CH_2$); 38.1 (CH); 103.1 (CH); 111.5 (CH); 114.3 (CH); 115.6 (CH); 116.6 (C); 117.8 (CH); 129.0 (CH); 132.6 (C); 144.1 (C); 145.2 (C); 151.8 (C); 157.4 (C); 167.8 (C=O) ppm.

Mass spectrum (EI): (%)=272 ($M^+$, 100); 254 (31); 229 (70); 213 (71); 162 (25); 115 (21); 77 (28); 63 (20); 51 (24); 39 (18).

Practical Example 1

Reduction of Bitterness of a Solution of Bitter Substance

In order to quantify the reduction (i.e. the masking or decrease) of the impression of bitterness in a sample, the bitterness of a solution containing 500 ppm caffeine or 200 ppm theobromine or 100 ppm naringin or 250 ppm salicin was compared by a panel of experts in each case with a sample that contained 500 ppm caffeine or 200 ppm theobromine or 100 ppm naringin or 250 ppm salicin and additionally the amount stated in each case of a substance to be assessed (with respect to capacity for reducing bitterness) (classification: 1 [not bitter] through 10 [extremely bitter]). The evaluation, i.e. calculation of the reduction (in %) of the impression of bitterness, was based in each case on the mean values of the appraisals of the panel of experts.

Practical Example 2

Reduction of Bitterness/Astringency of a Bitter Solution as a Function of Time

In order to quantify the reduction (i.e. the masking or decrease) of the impression of bitterness or astringency in a sample over a specified course of time, the bitterness, or astringency of a solution containing 750 ppm epigallocatechin gallate (EGCG) and 125 ppm ascorbic acid was compared by a panel of experts in each case with a sample that contained 750 ppm epigallocatechin gallate, 125 ppm ascorbic acid and additionally the amount stated in each case of a substance to be assessed (with respect to capacity for reducing bitterness), in this case a racemic mixture of compounds (7) and (8) (classification: 1 [not bitter] through 10 [extremely bitter]; or 1 [not astringent] through 10 [extremely astringent]). The panel's assessments were made at specified time points (10 seconds, 30 seconds, 50 seconds and 70 seconds after receiving the respective sample). The samples were assessed by the members of the panel one after another after neutralization. The evaluation, i.e. calculation of the reduction (in %) of the impression of bitterness/astringency was based at each measurement time point in each case on the mean values of the appraisals of the panel of experts for the epigallocatechin gallate solution and the sample to be compared, containing epigallocatechin gallate and a substance to be assessed.

| Test substance | Bitter substance | Time (s) | % reduction of the impression of bitterness | % reduction of the impression of astringency |
|---|---|---|---|---|
| 50 ppm (7) + (8) (ratio 1:1) | 750 ppm EGCG | 0 | −14% | −1% |

| Test substance | Bitter substance | Impression of bitterness (1-10) a) without test substance | Impression of bitterness (1-10) b) with test substance | % reduction of the impression of bitterness (significance) |
|---|---|---|---|---|
| 5 ppm (1) + (2) (ratio 1:1) | 100 ppm naringin | 5.5 ± 3.0 | 3.7 + 2.6 | 31.7% (p < 0.07) |
| 50 ppm (5) + (6) (ratio 1:1) | 500 ppm caffeine | 3.9 ± 1.7 | 3.0 ± 1.3 | 23.5% (p < 0.05) |
| 25 ppm (5) + (6) (ratio 1:1) | 300 ppm theobromine | 4.4 ± 1.5 | 3.1 ± 1.6 | 30.3% (p < 0.03) |
| 25 ppm (5) + (6) (ratio 1:1) | 100 ppm naringin | 6.1 ± 2.1 | 3.1 ± 1.4 | 49.0% (p < 0.0001) |
| 50 ppm (5) + (6) (ratio 1:1) | 250 ppm salicin | 6.6 ± 2.1 | 5.9 ± 2.5 | 11.1% |
| 25 ppm (7) + (8) (ratio 1:1) | 100 ppm naringin | 5.6 ± 2.5 | 2.9 ± 1.9 | 48.6% (p < 0.002) |
| 10 ppm (7) + (8) (ratio 1:1) | 300 ppm theobromine | 4.2 ± 2.2 | 3.6 ± 1.5 | 21.7% |
| 25 ppm (7) + (8) (ratio 1:1) | 500 ppm caffeine | 4.0 ± 2.0 | 3.4 ± 1.4 | 15.5% |
| 25 ppm (17) + (18) (ratio 1:1) | 100 ppm naringin | 5.3 ± 2.2 | 3.0 ± 1.6 | 44.3% (p < 0.01) |
| 25 ppm (23) + (24) (ratio 1:1) | 300 ppm theobromine | 4.5 ± 1.9 | 3.5 ± 1.6 | 22.4% (p < 0.1) |

-continued

| Test substance | Bitter substance | Time (s) | % reduction of the impression of bitterness | % reduction of the impression of astringency |
|---|---|---|---|---|
| | | 10 | −22%* | −7% |
| | | 30 | −25%* | −7% |
| | | 50 | −35%* | −19% |
| | | 70 | −29% | −15% |

*significant

Practical Example 3

Mixtures

| Ingredient | Mixture (amount used, wt %) | | | | | | | |
|---|---|---|---|---|---|---|---|---|
| | A | B | C | D | E | F | G | H |
| (7) + (8) (ratio 1:1) | 5 | 7 | 10 | 15 | 15 | 20 | 20 | 25 |
| Homoeriodictyol | 5 | | 2.5 | | | | | |
| Eriodictyol | | 2.5 | | | | | | |
| Phloretin | | | | 1 | | | | |
| Hesperetin | | | | | 0.5 | | | |
| 10 wt % trans-pellitorin (e.g. according to WO 2004/043906) in 1,2-propylene glycol/diethylmalonate | | | | 0.25 | 0.25 | 0.5 | 0.25 | |
| Extract of *Hydrangea macrophylla* according to EP 2 298 084 A1, containing phyllodulcin | 2.5 | | 2.5 | | | | | 2.5 |
| Extract of *Rubus suavissimus* containing rubusoside according to the European patent application with the application number 11 165 566.8 (Symrise) | | 2.5 | 2.5 | | | | | |
| 1,2-Propylene glycol | — | 20 | — | to 100 | to 100 | 20 | to 100 | — |
| Glycerol | — | to 100 | — | 20 | 20 | to 100 | 20 | — |
| Maltodextrin | to 100 | — | to 100 | — | — | — | — | to 100 |

The substances or solutions are mixed in the proportions stated above and then taken up in 1,2-propylene glycol and/or glycerol and completely dissolved by heating gently or mixed homogeneously with the solid carriers.

Practical Example 4

Spray-Dried Semifinished Product

| Ingredient | Amount used, wt % | | |
|---|---|---|---|
| | A | B | C |
| Drinking water | 60.8 | 60.8 | 60.8 |
| Maltodextrin from wheat | 24.3 | 24.3 | 24.3 |
| Gum arabic | 6.1 | 6.1 | 6.1 |
| (7) + (8) (ratio 1:1) | 8.8 | — | 4.4 |
| (3) + (4) (ratio 1:1) | — | 8.8 | 4.4 |

The drinking water was put in a vessel and the maltodextrin and gum arabic were dissolved therein. Then compound 1 and/or compound 2 were emulsified in the carrier solution using a Turrax. The temperature of the spraying solution should not exceed 30° C. The mixture was then spray-dried (required inlet temperature: 185-195° C., required outlet temperature: 70-75° C.). The resulting spray-dried semifinished products contained approx. 18-22% of compounds (7)+(8) and/or (3)+(4).

Practical Example 5

Tea Preparation

| | Amount used, wt % | | |
|---|---|---|---|
| | A | B | C |
| Black tea, Ceylon, leaf product | 94 | — | — |
| Green tea, China, leaf product | — | 92 | — |

-continued

| | Amount used, wt % | | |
|---|---|---|---|
| | A | B | C |
| Maté tea, Peru, leaf product | — | — | 95 |
| Mixture A from practical example 3 | 6 | — | — |
| Mixture B from practical example 3 | — | 8 | — |
| Mixture C from practical example 3 | — | — | 5 |

The tea and the semifinished product are mixed and packed in tea bags made of filter paper (2 g per filter bag). For use, a tea bag is steeped in 100-250 ml boiling water and left to draw for 2-5 min.

Practical Example 6

Black Tea Preparation

| Ingredient | Amount used, wt % |
|---|---|
| Black tea, Ceylon, leaf product | 94 |
| Mixture A from practical example 3 | 3 |
| Mixture B from practical example 3 | 3 |

The tea and the semifinished products are mixed and packed in tea bags made of filter paper (2 g per filter bag). For use, a tea bag is steeped in 100-250 ml boiling water and left to draw for 2-5 min.

Practical Example 7

Use in an Iced-Tea Beverage (Black Tea)

Compounds (7) and (8), or (3) and (4) were in each case dissolved beforehand at 10% in ethanol. Black tea extract was dissolved in water and stirred together with sugar, a flavor preparation (peach flavor), and the ethanolic solutions of compounds (7) and (8) (preparation A), or (3) and (4) (preparation B) in a beaker.

|  | Amount used, wt % | |
|---|---|---|
| Ingredient | A | B |
| Black tea extract | 1.4 | 1.4 |
| Water | 89.5 | 89.5 |
| Flavor preparation (peach type) | 0.67 | 0.67 |
| Sugar | 7 | 7 |
| Citric acid (crystalline) | 1.2 | 1.2 |
| Ascorbic acid | 0.2 | 0.2 |
| (7) and (8) in 1:1 ratio as 10% solution in ethanol | 0.03 | — |
| (3) and (4) in 1:1 ratio as 10% solution in ethanol | — | 0.03 |

Practical Example 8

Use in an Iced Tea Beverage (Green Tea, Reduced-Sugar)

Compounds (7) and (8) or (3) and (4) were in each case dissolved beforehand at 10% in ethanol. Green tea extract was dissolved in water and stirred together with sugar, and the sweetener saccharin or rebaudioside A, a flavor preparation (lemon flavor), and the ethanolic solutions of compounds (7) and (8) or (3) and (4) (preparation B) in a beaker.

|  | Amount used, wt % | |
|---|---|---|
| Ingredient | A | B |
| Green tea extract | 1.4 | 1.4 |
| Water | 92.95 | 93.03 |
| Flavor preparation (lemon type) | 0.65 | 0.65 |
| Sugar | 3.45 | 3.45 |
| Saccharin sweetener | 0.1 | — |
| Rebaudioside A sweetener | — | 0.02 |
| Citric acid (crystalline) | 1.2 | 1.2 |
| Ascorbic acid | 0.2 | 0.2 |
| (7) and (8) in 1:1 ratio, 10% solution in ethanol | 0.05 | — |
| (3) and (4) in 1:1 ratio, 10% solution in ethanol | — | 0.05 |

Practical Example 9

Use in an Iced Tea Beverage (Black Tea, Sugar-Free)

Compounds (7) and (8) or (3) and (4) were in each case dissolved beforehand in ethanol. Black tea extract was dissolved in water and stirred together with the sweetener saccharin, a flavor preparation (lemon flavor), and the ethanolic solutions of compounds (7) and (8) (preparation A), or (3) and (4) (preparation B) in a beaker.

|  | Amount used, wt % | |
|---|---|---|
| Ingredient | A | B |
| Black tea extract | 1.4 | 1.4 |
| Water | 96.465 | 96.465 |
| Saccharin | 0.035 | 0.035 |
| Flavor preparation (lemon type) | 0.65 | 0.65 |
| Citric acid (crystalline) | 1.2 | 1.2 |
| Ascorbic acid | 0.2 | 0.2 |
| (7) and (8) in 1:1 ratio, 10% solution in ethanol | 0.05 | — |
| (3) and (4) in 1:1 ratio, 10% solution in ethanol | — | 0.05 |

Practical Example 10

Use in a Soluble Cappuccino Beverage

The specified raw materials are mixed together. In each case 12.5 g of the instant cappuccino powder produced is dissolved in 150 ml of hot water.

|  | Amount used, wt % | | |
|---|---|---|---|
| Ingredient | A | B | C |
| Coffee extract, spray-dried | 18.0 | 18.0 | 16.0 |
| Sugar | 26.3 | 26.3 | 30.8 |
| Powdered fat | 18.2 | 18.2 | 18.2 |
| Coffee whitener, foaming | 30.0 | 30.0 | 28.0 |
| Hydrocolloids/emulsifiers | 1.8 | 1.8 | 1.8 |
| Lactose | 4.7 | 4.7 | 4.7 |
| Mixture A from practical example 3 | 1.0 | — | — |
| Mixture C from practical example 3 | — | 1.0 | — |
| Semifinished product C from practical example 4 | — | — | 0.5 |

Practical Example 11

Use in a Soybean Drink

Compounds (7) and (8) or (3) and (4) were in each case dissolved beforehand in ethanol and added to a soybean milk from a local supermarket. The mixture was stirred together with the milk flavoring in a beaker.

|  | Amount used, wt % | | | |
|---|---|---|---|---|
| Ingredient | A | B | C | D |
| Soybean milk (from local supermarket, unflavored, unsweetened) | 96.775 | 99.75 | 98.33 | 97.65 |
| Vanilla flavor | 0.1 | 0.1 | — | 0.05 |
| Milk flavor | — | — | 0.1 | 0.05 |
| Sucrose | 3.0 | — | 1.5 | 2.0 |
| Sucralose | — | 0.025 | 0.01 | — |
| Na-saccharin | — | — | 0.01 | — |
| Emulgum | 0.1 | 0.1 | — | 0.1 |
| (7) and (8) in 1:1 ratio, 10% solution in ethanol | 0.025 | — | 0.05 | — |
| (3) and (4) in 1:1 ratio, 10% solution in ethanol | — | 0.025 | — | 0.05 |
| Hesperetin, 5% in ethanol | — | — | — | 0.1 |

Practical Example 12

Use in a Soybean Drink in Combination with γ-Aminobutyric Acid

γ-Aminobutyric acid was dissolved beforehand in water and compounds (7) and (8) in ethanol and were added to a soybean milk from a local supermarket. The resulting mixture was stirred together with the milk flavoring in a beaker.

| Ingredient | Amount used, wt % |
|---|---|
| Soybean milk (from local supermarket) | 99.75 |
| Milk flavor | 0.1 |
| (7) and (8) in 1:1 ratio, 10% solution in ethanol | 0.05 |
| γ-Aminobutyric acid, 1% in water | 0.1 |

Practical Example 13

Use in a Grapefruit Juice

Compounds (7) and (8) were dissolved beforehand in ethanol and were added to a grapefruit juice from a local supermarket. The resulting mixture was homogenized in a beaker by stirring.

| Ingredient | Amount used, wt % |
|---|---|
| Grapefruit juice (from local supermarket) | 99.975 |
| (7) and (8) in 1:1 ratio, 10% in ethanol | 0.025 |

Practical Example 14

Use in a Bitter Chocolate

A bitter chocolate was made from the following raw materials and then cast in rectangular molds:

| Ingredient | Amount used, wt % | Amount used, wt % |
|---|---|---|
| Cocoa mass | to 100 | to 100 |
| Cocoa butter | 11.70 | 11.70 |
| Sugar | 29.50 | 29.50 |
| Skim milk | 3.00 | 3.00 |
| Lecithin | 0.2 | 0.2 |
| Vanillin | 0.035 | 0.035 |
| (7) and (8) in 1:1 ratio, 10% in ethanol | — | 0.025 |
| (3) and (4) in 1:1 ratio, 10% in ethanol | 0.05 | — |

Practical Example 15

Use in a Chewing Gum

| Part | Ingredient | Amount used, wt % |
|---|---|---|
| A | Chewing gum base, company "Jagum T" | 30.00 |
| B | Sorbitol, powdered | 39.00 |
|   | Isomalt ® (Palatinit GmbH) | 9.50 |
|   | Xylitol | 2.00 |
|   | Mannitol | 3.00 |
|   | Aspartame ® | 0.10 |
|   | Acesulfame ® K | 0.10 |
|   | Emulgum ® (Colloides Naturels, Inc.) | 0.30 |
| C | Sorbitol, 70% in water | 14.00 |
|   | Glycerol | 1.00 |
| D | Flavoring, containing 1% of compounds (7) and (8) in 1:1 ratio, relative to the total weight of the flavoring | 1.00 |

Parts A through D are mixed together and kneaded intensively. The raw mass can for example be processed in the form of thin strips to chewing gums ready for consumption.

Practical Example 16

Use in a Toothpaste

| Part | Ingredient | Amount used, wt % |
|---|---|---|
| A | Demineralized water | 21.50 |
|   | Sorbitol (70%) | 45.00 |
|   | Solbrol ® M, sodium salt (Bayer AG, p-hydroxybenzoic acid alkyl ester) | 0.15 |
|   | Trisodium phosphate | 0.10 |
|   | Saccharin, 450-fold | 0.20 |
|   | Sodium monofluorophosphate | 1.12 |
|   | Polyethylene glycol 1500 | 5.00 |
| B | Sident 9 (abrasive silicon dioxide) | 10.00 |
|   | Sident 22 S (thickening silicon dioxide) | 8.00 |
|   | Sodium carboxymethylcellulose | 0.90 |
|   | Titanium dioxide | 0.50 |
| C | Demineralized water | 4.53 |
|   | Sodium lauryl sulfate | 1.50 |
| D | Flavoring, containing 1 wt % of compounds (7) and (8) in 1:1 ratio, relative to the total weight of the flavoring | 1.50 |

The ingredients of parts A and B are in each case mixed first individually and then stirred well together under vacuum at 25-30° C. for 30 min. Part C is mixed beforehand and added to A and B; D is added and the mixture is stirred well under vacuum at 25-30° C. for 30 min. After returning to normal pressure, the toothpaste is ready and can be filled.

The invention claimed is:

1. A method of masking one or more bitter, astringent and/or metallic tastes of one or more bitter, astringent and/or metallic tasting substances comprising mixing:
one or more bitter, astringent and/or metallic tasting substances selected from the group consisting of caffeine, theobromine, quinine, salicin, arbutin, neohesperedin, eriocitrin, neoeriocitrin, narirutin, naringin, phloridzin, catechin, epicatechin, epigallocatechin gallate (EGCG), gallocatechin, gallocatechin-3-gallate, procyanidin B2, procyanidin B5, procyanidin C1, thearubigenin, rutin, taxifolin, nomilin, myricetin, myrictrin, caffeic acid or esters thereof, nomilin, an amino acid, a peptide with an amino acid of leucine, isoleucine, valine, tryptophan, proline or phenylalanine on the N- or C-terminus, potassium chloride, paracetamol, aspirin and a β-lactam antibiotic; with 5 to 200 ppm of one or more compounds of formula (I), or a physiologically acceptable salt thereof,

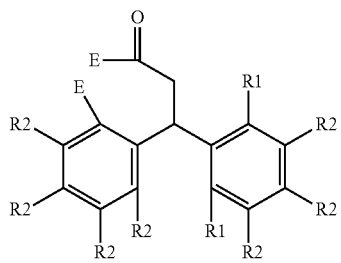

(I)

wherein,
E each denote OH or both E together denote oxygen,
R1, in each case independently of the other residue R1, denotes hydrogen or OR$^a$, wherein R$^a$ is hydrogen, C1-C5 alkyl or C2-C5 alkenyl,
R2, independently of the other residues R2, denotes hydrogen or OR$^b$, wherein R$^b$ is hydrogen, C1-C5 alkyl or C2-C5 alkenyl,
wherein optionally two directly adjacent residues R1 and/or R2 together represent a group OCH$_2$O; and
wherein the amount of the one or more bitter, astringent and/or metallic tasting substances is sufficient to be perceived as a bitter, astringent and/or metallic in comparison to a comparative preparation, that contains neither a compound of formula (I) nor a salt of a compound of formula (I), but is otherwise identical in composition;
thereby masking the one or more bitter, astringent and/or metallic tastes of one or more bitter, astringent and/or metallic tasting substances.

2. The method according to claim 1, wherein
R1, in each case independently of the other residue R1, denotes hydrogen or hydroxyl,
R2, independently of the other residues R2, denotes hydrogen, hydroxyl, methoxy, ethoxy, n-propoxy, iso-propoxy, n-butoxy, iso-butoxy, tert-butoxy or OR$^b$, wherein R$^b$ is C5 alkenyl.

3. The method according to claim 1, wherein the one or more compounds of formula (I), or physiologically acceptable salt thereof, is one or more compounds formula (II), or a physiologically acceptable salt thereof,

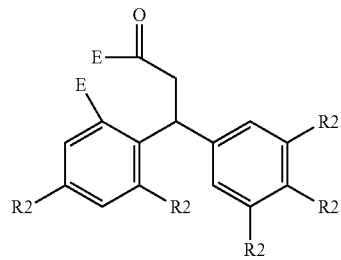

(II)

wherein
E each denote OH or both E together denote oxygen,
R2, independently of the other residues R2, denotes hydrogen, hydroxyl, methoxy, ethoxy, n-propoxy or iso-propoxy,
wherein optionally two directly adjacent residues R2 together represent a group OCH$_2$O.

4. The method according to claim 1, wherein the one or more compounds of formula (I) are selected from the group consisting of:

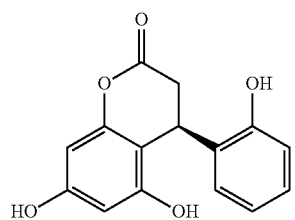
(1)

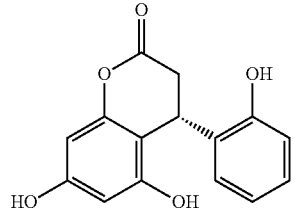
(2)

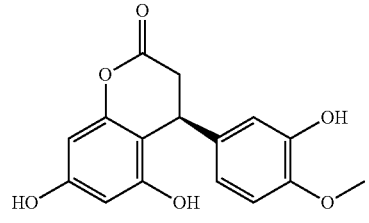
(3)

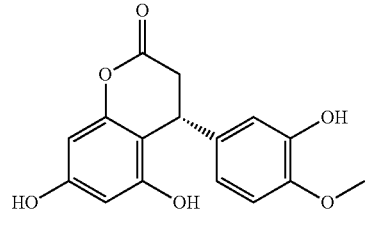
(4)

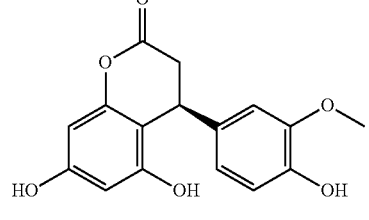
(5)

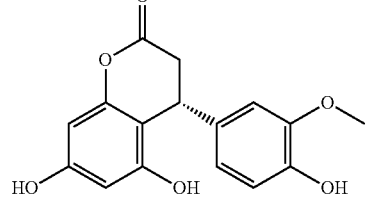
(6)

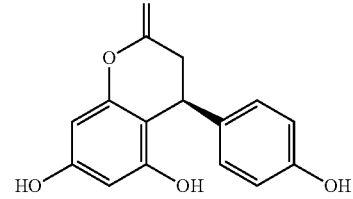
(7)

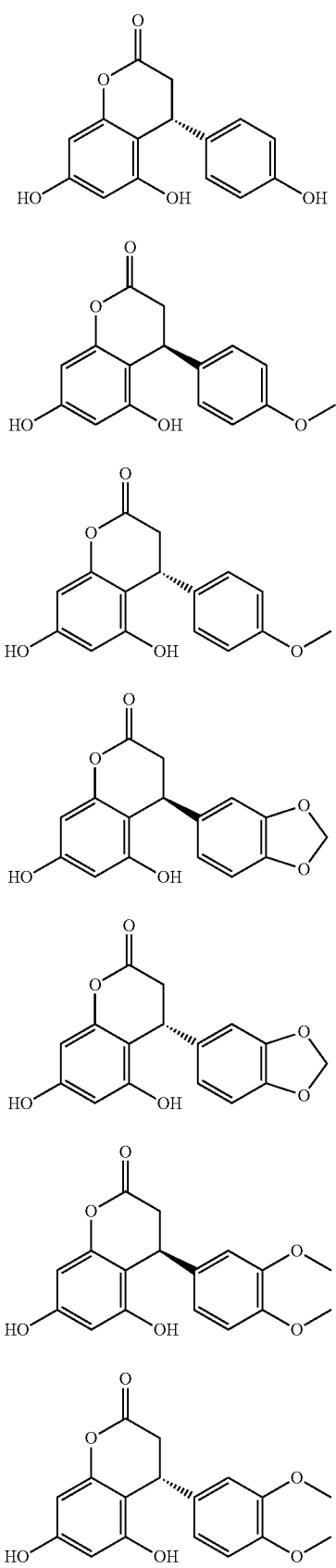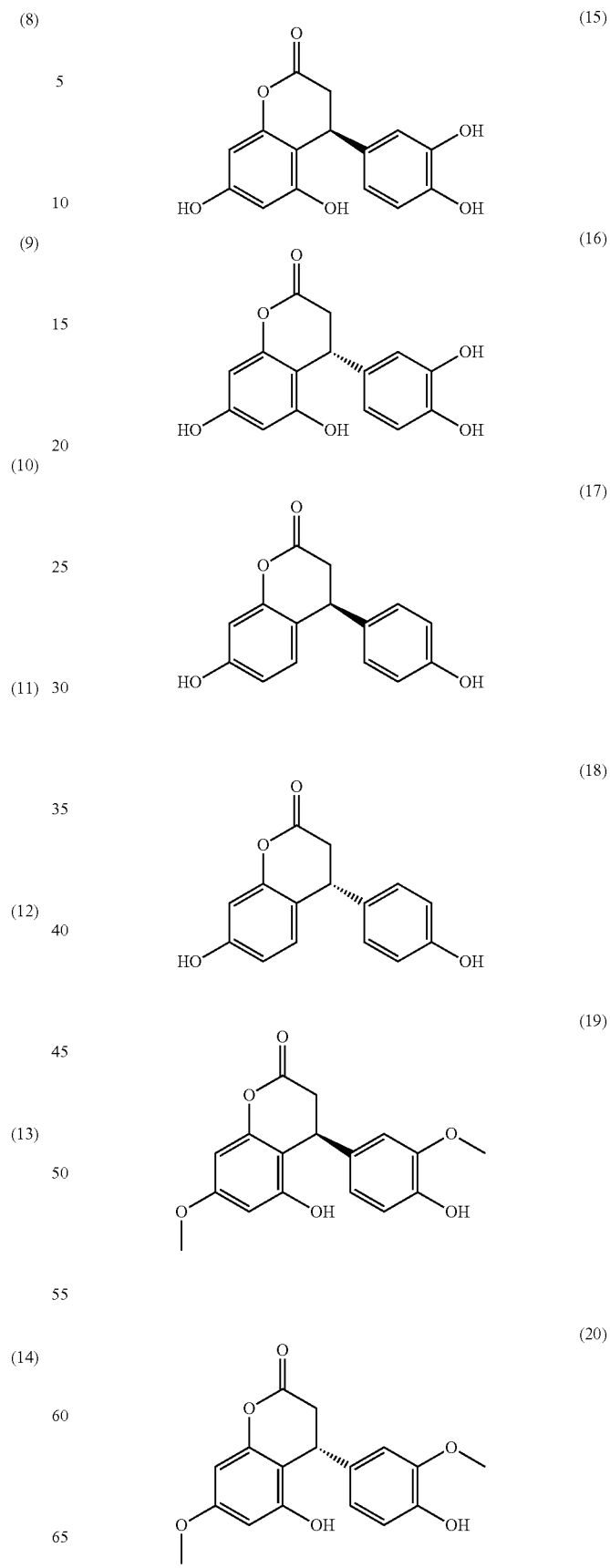

(21) 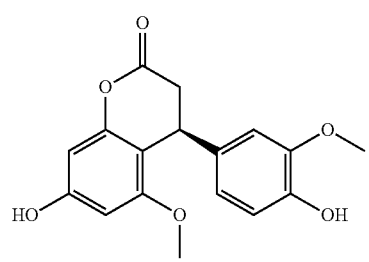
(22) 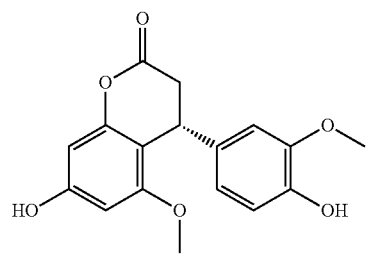
(23) 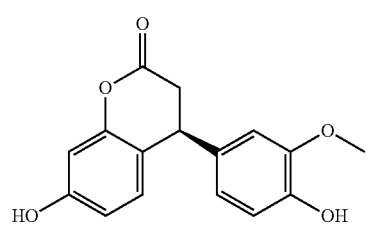
(24) 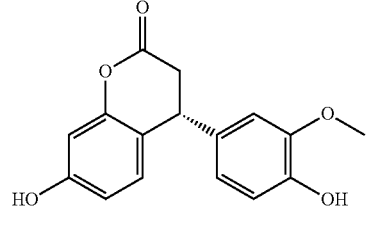
(25) 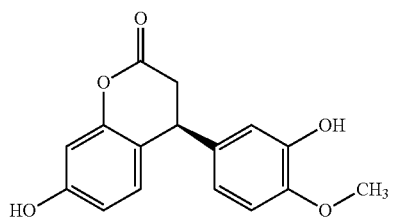
(26) 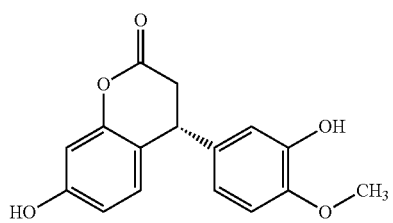
(27) 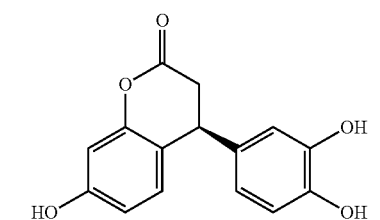
(28) 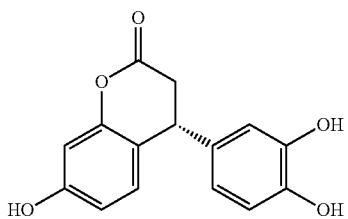
(29) 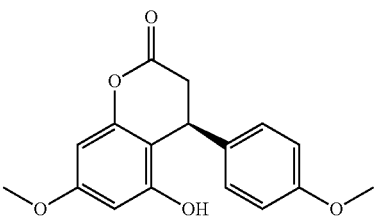
(30) 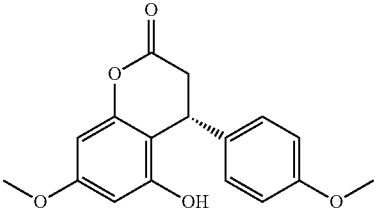
(31) 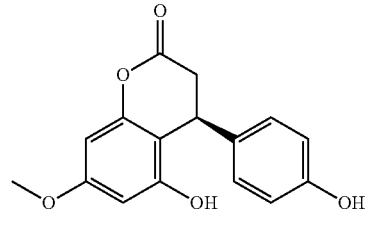
(32) 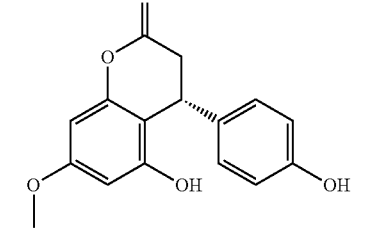
(33) 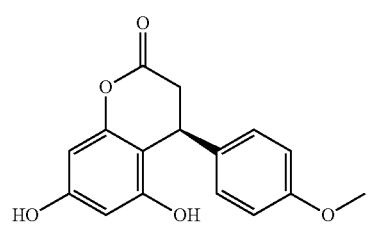
(34) 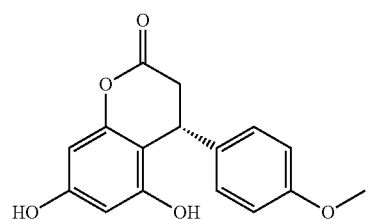

-continued

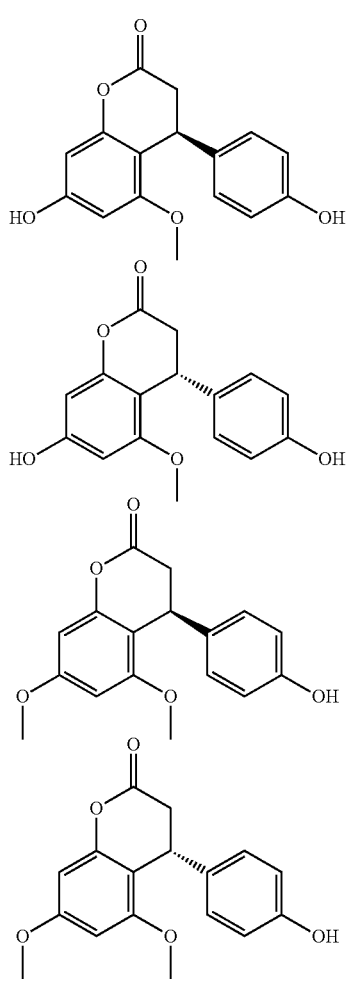

(35)
(36)
(37)
(38)

-continued

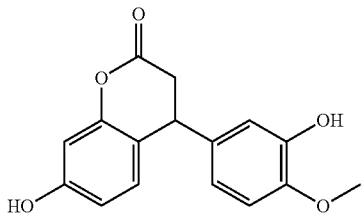

(39)

and

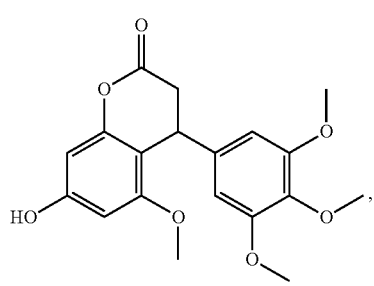

(40)

or a physiologically acceptable salt thereof.

5. The method according to claim 1 comprising mixing one or more physiologically acceptable salts of a compound of formula (I) with one or more bitter, astringent and/or metallic tasting substances, wherein an oppositely charged cation for the one or more physiologically acceptable salts is present and is selected from the group consisting of $Na^+$, $K^+$, $NH_4^+$, $Ca^{2+}$, $Mg^{2+}$, $Al^{3+}$ and $Zn^{2+}$.

6. The method as claimed in claim 1, further comprising mixing a further aromatic substance with a molecular weight above 90 g/mol.

* * * * *